United States Patent [19]

Colgate et al.

[11] Patent Number: 5,410,638
[45] Date of Patent: Apr. 25, 1995

[54] SYSTEM FOR POSITIONING A MEDICAL INSTRUMENT WITHIN A BIOTIC STRUCTURE USING A MICROMANIPULATOR

[75] Inventors: Ledward Colgate, Evanston; Mathew R. Glucksberg, Chicago; Kenneth W. Grace, Evanston, all of Ill.

[73] Assignee: Northwestern University, Evanston, Ill.

[21] Appl. No.: 56,479

[22] Filed: May 3, 1993

[51] Int. Cl.⁶ .............................................. G06F 15/00
[52] U.S. Cl. ........................................ 395/99; 395/89; 395/95; 395/97
[58] Field of Search ...................... 395/89, 92, 95, 97, 395/99

[56] References Cited

U.S. PATENT DOCUMENTS

| | | | |
|---|---|---|---|
| 3,909,600 | 9/1975 | Hohn | 395/86 |
| 3,923,166 | 12/1975 | Fletcher et al. | 395/89 |
| 4,132,318 | 1/1977 | Wang et al. | 414/591 |
| 4,342,951 | 8/1982 | Muller et al. | 318/625 |
| 4,520,816 | 6/1985 | Schachar et al. | 606/4 |
| 4,526,447 | 7/1985 | Taylor | 359/196 |
| 4,635,206 | 1/1987 | Bhatia et al. | 395/89 |
| 4,676,002 | 6/1987 | Slocum | 33/1 MP |
| 4,694,230 | 9/1987 | Slocum et al. | 318/568.17 |
| 4,749,270 | 6/1988 | Endo et al. | 359/392 |
| 4,907,158 | 3/1990 | Kettler et al. | 364/413 A |
| 4,925,284 | 5/1990 | Ward et al. | 359/393 |
| 4,972,347 | 11/1990 | Tarvin et al. | 395/89 |
| 5,007,300 | 4/1991 | Sira | 74/471 |
| 5,053,687 | 10/1991 | Merlet | 318/568.2 |
| 5,116,180 | 5/1992 | Fung et al. | 414/5 |

OTHER PUBLICATIONS

Controlling Remote Manipulators Through Kinesthetic Coupling A. K. Bejcey et al., 1983 Jul. 31.
Electrostatic Micro Manipulator with 6 D.O.F. of Fukuda et al. IEEE/3–5 Nov. 1991.
Analysis of a Fully-Parallel Six Degree-of-Freedom Micromanipulator Hudgens et al. IEEE 19–22 Jun. 1991.
Pournaras, Constantin J. et al., *New Ocular Micromanipulator for Measurements of Retinal and Vitreous Physiologic Parameters in the Mammalian Eye*, University of Geneva, Geneva, Switzerland and University of Pennsylvania, PA (Aug. 27, 1990).
Merlet, J-P., *Direct Kinematics and Assembly Modes of Parallel Manipulators*, The International Journal of Robotics Research, vol. II, No. 2 (Apr., 1992).

Primary Examiner—Allen R. MacDonald
Assistant Examiner—Richemond Dorvil
Attorney, Agent, or Firm—Welsh & Katz, Ltd.

[57] ABSTRACT

A device is provided for precision positioning of a medical instrument within a biotic structure through a hole in an exterior wall of the biotic structure. A structural member of the instrument extends through the hole of the biotic structure at a puncture point with the instrument disposed on the structural member at a first end within the biotic structure. A medical instrument holder disposed at a second end of the structural member outside the biotic structure is provided for retaining a medical instrument at a predetermined angle. The device also includes instrument manipulating apparatus for supporting and positioning the instrument holder to position the medical instrument at the desired location while maintaining the structural member substantially stationary in the plane of the exterior wall at the puncture point. A selectively moveable support has legs that are independently pivotally rotatable about a joint, such as a ball and socket joint. The moveable support is coupled to actuators for activating the selectively moveable support. An input device, which generates a positioning signal that corresponds to the surgeon's desired positioning of the medical instrument, is also included. A computer for controlling the actuators determines the correct movement of the selectively moveable support based on the electronic signal of the input device, which thereby positions the medical instrument at the correct location.

31 Claims, 6 Drawing Sheets

SYSTEM FOR POSITIONING A MEDICAL INSTRUMENT WITHIN A BIOTIC STRUCTURE USING A MICROMANIPULATOR

This invention relates generally to high-precision instrumentation and more specifically to a system for controlling, via an input device, the positioning of an instrument attached to a precision micromanipulator particularly suitable for microsurgery.

BACKGROUND OF THE INVENTION

Micromanipulation, which uses a micromanipulator to effect the techniques and science of microdissection, microvivisection, microisolation, and microinjections, is an expanding area which is generating a considerable amount of interest in the medical science field. Micromanipulators are well known in the art and there are various theoretical and actual embodiments of micromanipulators.

Micromanipulators or micropositioners are instruments of great precision with which a microneedle, micropipette, or other microtool can be positioned in the field of a microscope within the area to be worked upon. Currently known micromanipulators are instruments which range from simple rack and pinion assemblies to massive, accurately fitted ball bearing slide mechanisms actuated by precise feed screws or other devices. Other micromanipulators are lever-controlled and use coaxial knobs or handle mechanisms. Some available micromanipulators are hydraulically or pneumatically actuated or are piezo-electrically actuated. A well known micromanipulator is the Leitz micromanipulator.

A variety of procedures occurring in surgery and in biomedical research require positioning of microinstruments within a position of a few microns or less. Examples include treatments for retinal detachment, retinal vasculitis, and retinal artery and vein obstruction. Positioning such instruments for these tasks is generally achieved manually without a micromanipulator. The utility of conventional and currently available micromanipulators is limited by either an insufficient number of degrees of freedom or its bulk (i.e. size and weight). Though micromanipulators are commercially available, nearly all micromanipulators work by translation in a Cartesian system (i.e. X, Y and Z axes), and therefore, are unsuitable for intra-ocular surgical procedures or other procedures or applications that require the microtool to be constrained by a physical puncture point or some other determined point.

While Cartesian micromanipulators may provide precision and do have up to three degrees of freedom (in the hands of a skilled operator, controlled motions of well under five microns are readily available) they are nevertheless centerless. In other words, they do not work when the motion of the micromanipulator is constrained, as through a puncture hole in the eye. Thus, any displacement of the microtool tip will be accompanied by an equal displacement of every other point on the micromanipulator, which can cause trauma to the area surrounding the puncture point.

One field in which micromanipulation is of great interest and import is in the area of ocular surgery, particularly, retinal vascular diseases or vascular complications. Because vascular diseases or complications, (including conditions arising from diabetes and hypertension) account for a majority of all vision impairing conditions, there is a significant need for surgical instruments to permit direct access to retinal vessels (e.g. injection of medications directly into the retinal vessels). A system capable of microinjection into a single vessel would permit development of entirely new areas of treatment for retinal vascular disorders. However, control of the positioning of prior art micromanipulators has been limited by the ability of the surgeon to adjust the micromanipulators by hand using a system of wheels, gears and screws.

The limitations involved with currently available micromanipulators is especially acute for ophthalmologists who routinely place instruments inside the eye during surgery and frequently do so through a puncture in the sclera. In such procedures (e.g. vitrectomies), the inability of the surgeon to position the microtool tip with sufficient precision and maintain it is a serious limitation. The delicate nature and small diameter (approximately 100–200 $\mu$m) of the retinal vessels requires an extremely precise micromanipulator which can direct a microtool within the eye, while being able to move the microtool with increased freedom without increased trauma to the eye.

Further, the positioning of the microtool tip should not affect the point where the instrument actually passes through or punctures the sclera to minimize trauma to the eyeball. Prior art micromanipulators are not suitable for such surgical manipulation since the motion of the microtool must be constrained by the puncture point, such as in the sclera of the eye. Consequently, there is a need for a micromanipulator which works in a spherical (i.e. goniometric) fashion, where the entire surgical instrument is constrained by and rotates about the puncture point or other fixed location.

To provide increased precision and flexibility, there is a need for a computer based system wherein the surgeon's hand movements are translated through an input device to correspond to the desired microtool tip positioning and movement. Thus, manual adjustments to a computer input device (e.g. joystick) which correspond to changes in the position of the microtool tip may be determined and performed by the computer system. Accordingly, the translation of the surgeon's hand movements to microtool tip positioning becomes transparent to the surgeon.

There is also a need to provide a micromanipulator and control system that has increased flexibility by allowing increased degrees of freedom for micromanipulation or other applications. There is further a need for a compact, lightweight, easy-to-use micromanipulator which can be used for ocular surgical procedures on the human eye, while having at least six degrees of freedom and remain versatile enough to be used on both medical or non-medical applications.

Accordingly, an object of the present invention is to provide a micromanipulator that is compact, relatively light-weight, and versatile which provides the user with at least six degrees of freedom for positioning the micromanipulator with precision and which is suitable for use in both medical and non-medical applications.

Another object of the present invention is to provide a computer system which translates a surgeon's input signals or indicia to relative movement of a microtool tip through the appropriate adjustment of a micromanipulator when the microtool is physically or otherwise intentionally constrained at a point.

Yet another object of the present invention is to provide a compact, high-precision micromanipulator system which permits a surgeon to control a micromanipulator tool centered on a single puncture point, while the adjustment of the micromanipulator to effectuate the movement and positioning of the microtool tip is performed by a computer system transparent to the surgeon.

The above-identified objects, as well as others not specifically iterated, are achieved in accordance with embodiment of the present invention wherein a device for precision positioning of a medical instrument includes a medical instrument holder for retaining a medical instrument at a predetermined angle. The device also includes instrument manipulating apparatus for supporting and positioning the instrument holder to position the medical instrument at the desired location. The instrument manipulating apparatus is mounted on a selectively moveable support having legs that are independently pivotally rotatable about a joint, such as a ball and socket joint. The moveable support is coupled to actuators for activating the selectively moveable support. An input device, which generates a positioning signal that corresponds to the surgeon's desired positioning of the medical instrument, is also included. A computer for controlling the actuators determines the correct movement of the selectively moveable support based on the electronic signal of the input device, which thereby positions the medical instrument at the correct location.

SUMMARY

An apparatus is provided for positioning an instrument within a biotic structure through a hole in an exterior wall of the biotic structure. A structural member of the instrument extends through the hole of the biotic structure at a puncture point with the instrument disposed on the structural member at a first end within the biotic structure. An articulated manipulator means disposed at a second end of the structural member, external to the biotic structure, is provided for positioning the instrument while maintaining the structural member substantially stationary in the plane of the exterior wall at the puncture point.

BRIEF DESCRIPTION OF THE DRAWINGS

Further objects of the invention, together with additional features contributing thereto and advantages occurring therefrom, will be apparent from the following description of embodiments of the invention when read in conjunction with the accompanying drawings, wherein.

DETAILED DESCRIPTION OF THE PREFERRED EMBODIMENT

A portion of the disclosure of the patent document, including Appendix A, contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Figure 1:
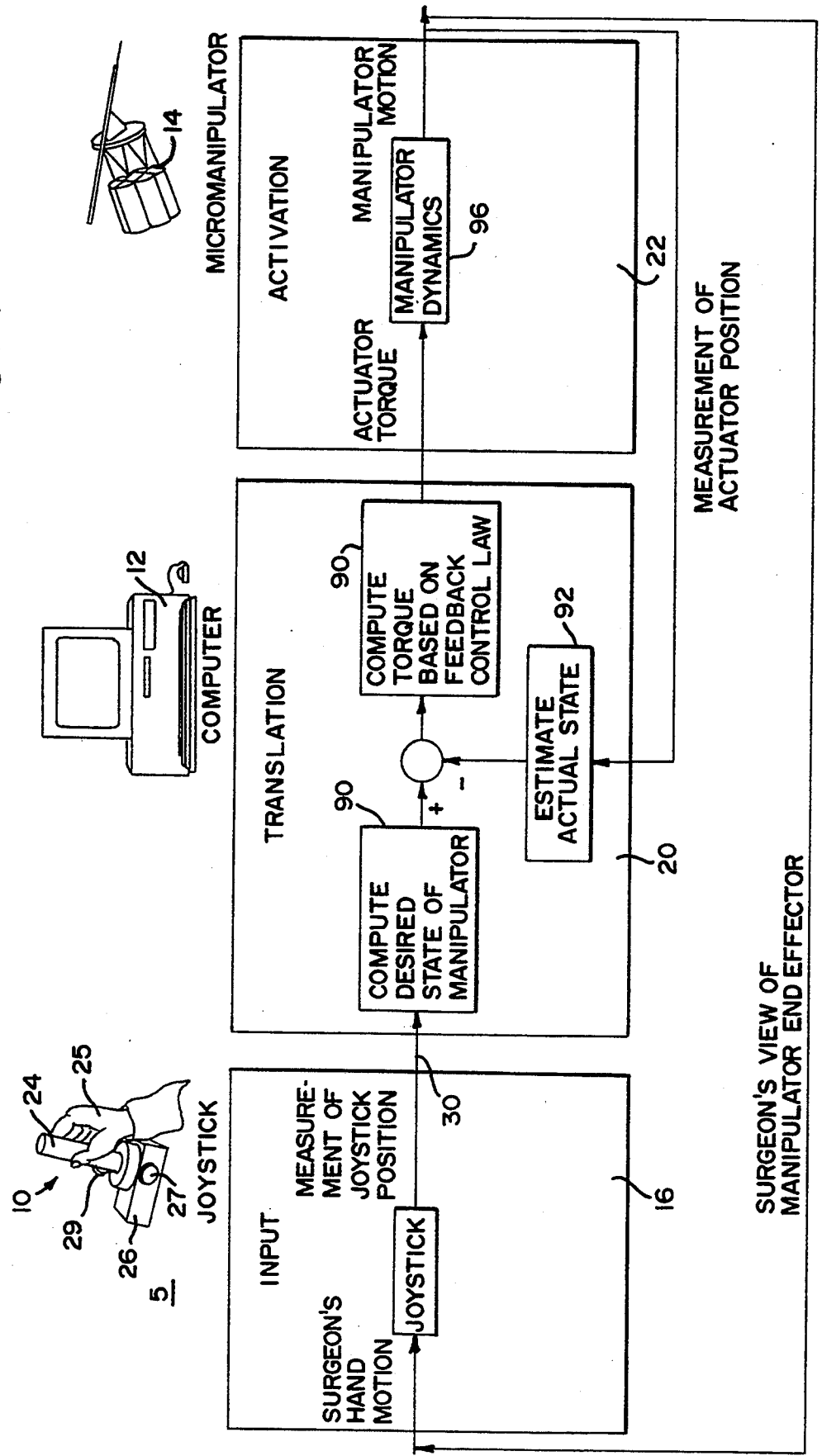
FIG. 1 is a general, overall schematic of the control flow for one embodiment of the present invention depicting the three main segments of the system.

Referring now to FIG. 1, there is shown an overview schematic representation of the system 5 of the present invention for positioning an instrument within a biotic structure depicting an input device 10, a computing device 12 (e.g. personal computer) and a micromanipulator device 14. Each device 10, 12 and 14 of the present system also corresponds to a specific section within the overall system 5 comprising an input system 16, a translation section 20 and an activation section 22. The computing device 12 in the illustrated embodiment is an industry standard architecture (ISA) IBM compatible personal computer using an Intel 486 CPU. However, the computing device 12 may be any suitable circuitry for performing the require calculation, translation and control functions including an application specific integrated circuit (ASIC) designed specifically to implement the invention.

The contemplated input device 10, represents the hardware for the input section 16, which can for example be a joystick device, wherein the surgeon's hand motion, which represents the desired motion and positioning of the micromanipulator 14, is obtained for translation and realization of the desired movement by the computer 12. Accordingly, a movement of the joystick is translated to control signals which generate corresponding movement of the micromanipulator 14. Essentially an electronic input signal generated by the joystick, or other input device 10, is utilized by the computer 12 to determine how the micromanipulator 14 should be activated or adjusted to correspond to the surgeon's desired new location (state) for the micromanipulator 14, based on how the micromanipulator 14 is presently positioned.

Within the translation section 20, the computer 12 accepts the desired location (i.e. state) for the micromanipulator 14 in the form of an electronic signal from the device 10 of the input section 16, which is generated by the surgeon's manual movement of the device 10. The computer 12 then computes the desired state of the micromanipulator 14 through a translation routine which will be described in detail hereinafter. Thus, the computer 12 computes the movement required to translate the surgeon's hand motion to the required activation of the components of the micromanipulator 14 to arrive at the desired state.

In the activation section 22, mechanisms (e.g. actuators 64 shown in FIG. 2) of the micromanipulator 14 are activated to produce the desired motion imputed by the surgeon in the input section 16. This section 22 of the schematic represents the fact that the micromanipulator 14 responds to the surgeon's hand motion in response to control signals generated by the computer section 20.

The motion of the micromanipulator 14 is cycle based. One full cycle (e.g. approximately every 1 millisecond in the illustrated embodiment) is completed based on the surgeon's manipulation and then another cycle begins again with a new sampling of the movement indicated by the input device 10 (e.g. movement caused by the surgeon's manual movement of a joystick). Prior to the completion of the cycle, the current state of the actuators 64 is detected by sensors (e.g. resolvers 66 in FIG. 3) which measure the actuator position and velocity for comparison with the surgeons's desired state of the micromanipulator 14. Also, for completeness of the cycle, FIG. 1 also shows the surgeon's visual feedback of the movement and present position of a microtool 44 (shown in FIG. 2) mounted on the micromanipulator 14. The present system 5 does not limit the surgeon's movement of the microtool 44 with input device 10. Instead, the surgeon sees the micromanipulator 14 and the microtool 44 move in synchronicity with his hand motions and therefore the intervening control system is transparent to the surgeon.

Figure 5:
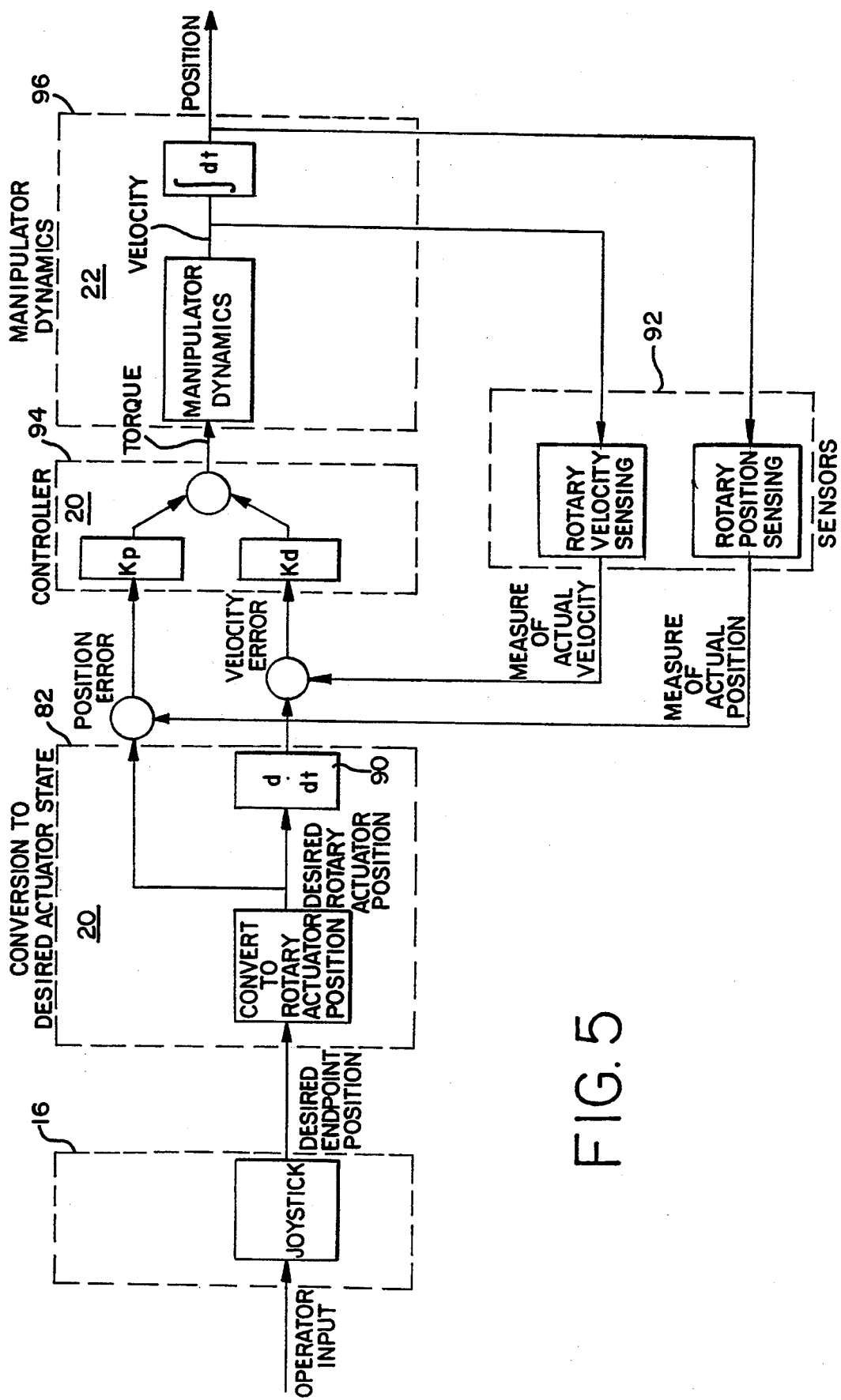
FIG. 5 depicts, with even more specificity, the control flow of one embodiment of the present invention from the surgeon's hand input through the computer translation to activation of the micromanipulator.

As stated above, in one embodiment, the input device 10 of the input section 16 may be a conventional joystick. As shown in FIGS. 1 and 5, the joystick includes a generally elongated handle section 24 which is pivotally coupled to a base support 26. The handle 24 is configured to be held by a human hand 25 and is pivotally moveable about X and Y axes with respect to the connector point 28 with the base support 26. The base support 26 of the joystick includes conventional electronic signal generating hardware (not shown) that generates electronic signals that correspond to the movements of the handle 24 in the X and Y directions, and communicates them electronically over the input line 30 to the computer 12.

The input device 10, such as joystick, may include a sensitivity adjustment 27, which can be adjusted to translate the surgeon's hand motion proportionally via the electronic signals to the computer 12 and then to micromanipulator 14. A plunge activation control 29 (e.g. a thumb-wheel on the joystick) may also be included to provide a third control input to permit control of the "plunge" or axial movement of the micropipette 50.

It is important to realize that input device 10 need not be limited to the joystick, but it is contemplated that any other suitable input devices, such as a computer mouse, stylus pen, digitizer, computer glove, keyboard or other similar input devices, can be utilized. In fact, it is contemplated that the hand held activation input device 10 could be replaced with a voice activated system or the like as such systems are developed. It is sufficient that the input device 10 provides the user with the ability to transmit via some form of indicia the desired movement of the microtool 44.

Figure 2:
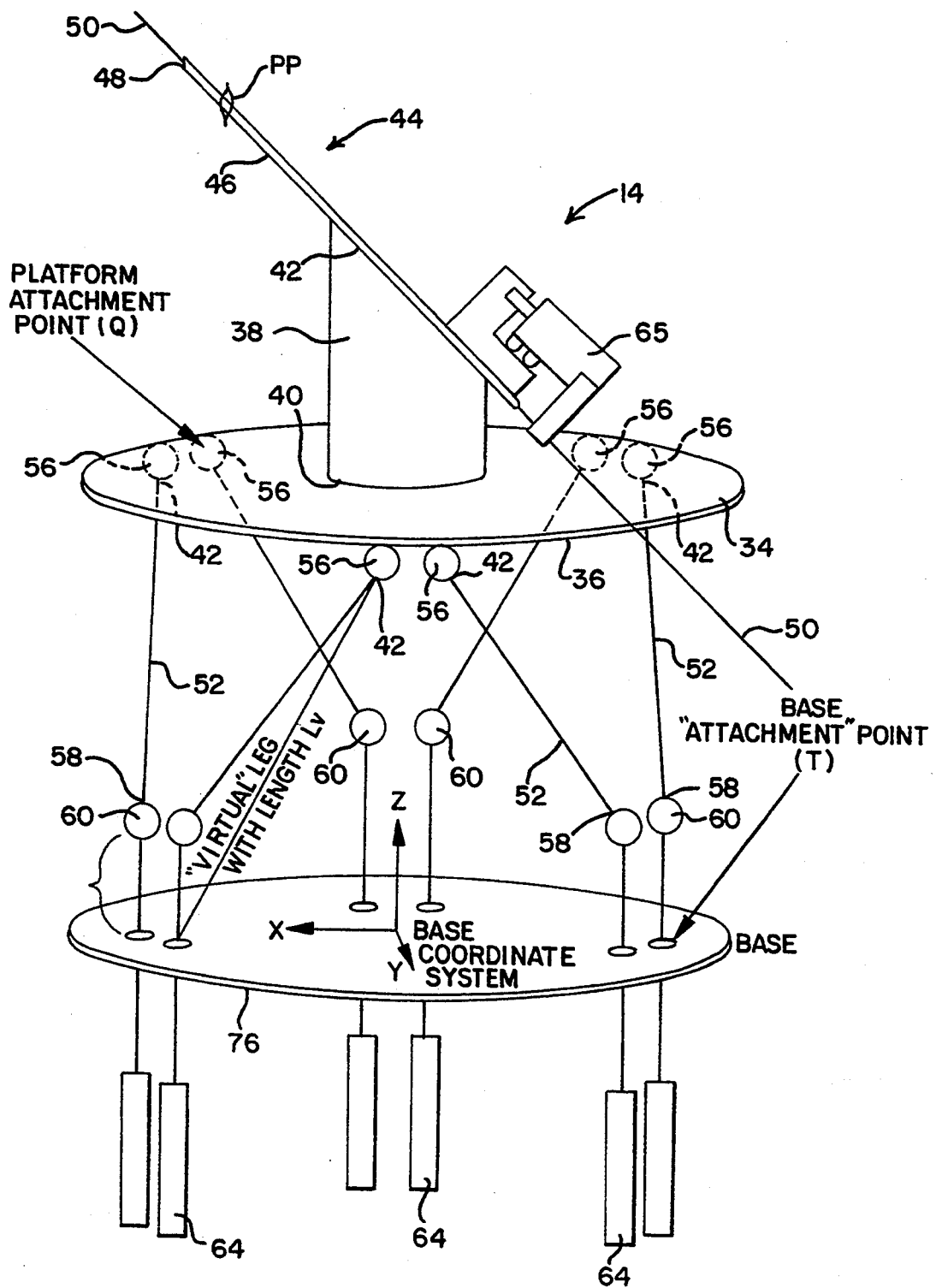
FIG. 2 is a graphical representation of a typical micromanipulator for use with a micromanipulator control system according to the invention.

Shown most clearly in FIG. 2 (see also FIGS. 1 and 5), is one embodiment of the micromanipulator 14 with a mechanical structure having several components. It should be understood that the present invention is contemplated for use with any appropriate micromanipulator 14, which is designed to function within the requirements of the input section 16, translation section 20 and activation section 22. However, in the illustrated embodiment the micromanipulator 14 is configured as a parallel mechanism having an attachment platform 32, which is shown to be generally circular, but can take on any desired shape.

The attachment platform 32 is typically solid and has an upper surface 34 and a lower surface 36. Mounted to the upper surface 34 or integral therewith, is a microtool connector 38 mounted thereon along its lower end 40. The upper end 42 of the microtool connector 38 is an angled surface configured to accept and retain a microtool 44, such as a needle 46 having an effectuator end or working end 48. An effectuator end 48 is any type of instrument or tool end for performing a task. In the illustrated embodiment, the effectuator end is shown and described as a micropipette 50, but other types of needles, injectors, probes, lenses and the like are contemplated. The needle 46 provides a structural element linking the instrument and micromanipulator and is used to gain access to the desired inner portion of the eye or other area of the biotic structure through a hole in an exterior wall such as a puncture point PP in the surface of the eye, typically through the sclera. (See FIG. 6).

The puncture point PP is the intended intersection of the needle 46 and the sclera during normal operation. This is a fixed point on the needle 46 regardless of where the needle 46 is positioned. Once the micromanipulator 14 is positioned for surgery, the entire platform 32 of the micromanipulator 14 will pivot about this puncture point PP maintaining the needle substantially stationary in a plane of the exterior wall of the sclera as if the puncture point PP were fixed in space.

The micropipette 50 is typically a rigid glass tube which is disposed within the needle 46 and can be moved axially in and out of the end 50 of the needle 46. The needle 46 is typically a hollowed steel tube which acts as a conduit for the vertical movement of the micropipette 50 or some other micro-surgical instrument. The micropipette 50 is used to puncture the desired vessel within the eye to introduce a given drug into the vessel, such as to dissolve blood clots formed in the retinal vessels in the back of the eye. (See FIG. 6). Although a conventional micropipette 50 is here shown and described, other microtools such as needles, hooks, loops or other effectuators or working ends used in microsurgery can be adapted for use within the present invention without detracting from the principles stated herein.

The upper end 42 of the microtool connector 38 is shown having a 45° angle, which has been found to give a surgeon the best combination of range of motion and sensitivity once constrained, such as through the sclera of the eye, and to facilitate loading the micropipette 50. The preferred 45° angle, together with the compact size of the micromanipulator 14, also facilitates the positioning and entry of more than one microtool 44 with more than one micromanipulator 14. Accordingly, the angle of the upper end 42 may be different based on the application or configuration of the micromanipulator 14.

Attached to the lower surface 36 of the attachment platform 32 are the legs 52 which are of a fixed length FL in the illustrated embodiment. It is also contemplated that other leg designs may be adapted to the present invention, such as adjustable legs or legs having different lengths. As shown, there are at least six legs 52 having length FL in the illustrated embodiment. Each leg 52 is pivotally, movably coupled at their upper end 42 to the lower surface 36 by a system of upper ball joints 56. This point of attachment between the legs 52 and platform 32 is also designed as point "Q" and will be referred to later in the discussion of the translation section 20. In the illustrated embodiment, each leg 52 is independently moveable with respect to each other. Also, although six legs 52 are shown and described here, it will be understood that additional legs 52 and actuators 64 may be utilized for the present system 5.

Each leg 52 also has a lower end 58 which is pivotally, movably coupled to another set of ball joints 60. This point of "attachment" is also referred to as point "T" is a virtual attachment point, which will be discussed later in this description. The lower ball joints 60 are fixedly coupled to actuator extension arms 62 that are each in turn fixedly secured to an actuator 64. Each actuator 64 is, in the illustrated embodiment, preferably a motor actuated ball screw linear slider combination (shown in FIG. 3), but hydraulic or pneumatically driven systems that can be controlled by the computer 12 are also contemplated. The computer 12 computes the necessary movement and generates the corresponding control signals required to move each actuator 64 to generate the appropriate movement of the legs 52. This results in the movement of the attachment platform 32, the connector 38 and therefore needle 46 and effectuator end 48 to correspond to the surgeon's movement of the joystick for positioning the effectuator end 48 where desired by the surgeon.

Figure 3:
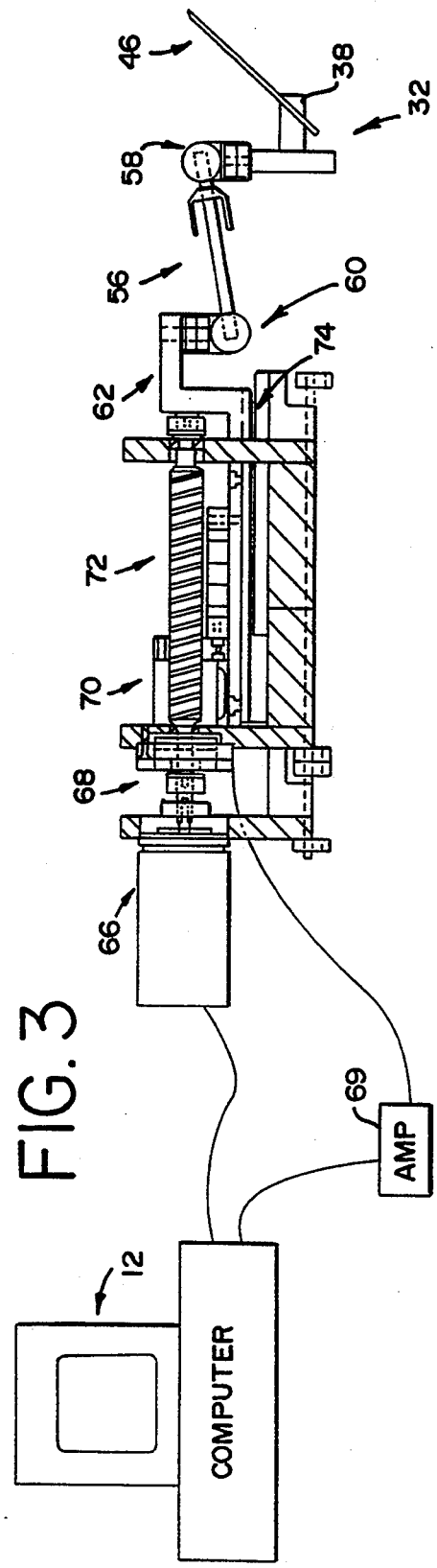
FIG. 3 depicts an actuator of the type suitable for use with the invention.

A suitable actuator 64 illustrated in FIG. 3 has a conventional analog driver amplifier 69 (e.g. Model EM19-28030-B01 marketed by Inland Motor, 501First Street, Radford, Va.), which transforms the electronic signals delivered by the computer 12 into drive signals to activate a motor 68 (e.g. Model QT-0717-D marketed by Inland Motor, 501 First Street, Radford, Va.). A conventional resolver 66 is provided to detect the motor motion and generate corresponding electric position and velocity signals. The activation/deactivation and forward/reverse activation of the motor 68 generates mechanical motion that is transferred to a ballnut 70 which in turn transfer the motion to the ballscrew 72. The ballscrew 72 then causes the linear slider assembly 74 together with arms 62 to extend or detract from its position as is well known in the art. This causes pivoting action at the ball joints 56 and 60 to move the leg 52 and thereby raise or lower the platform 32.

With six legs 52 and six actuators 64 there are six attachment points T. Six degrees of freedom of movement for the platform 32 is attained through this illustrated construction. Each actuator 64 effects its own leg 52 independently of the others and the combination of leg 52 positions dictated by the computer 12 through the actuator 64 based on the input from input device 10 creates a unique position of the effectuator end 48, with respect to the fixed puncture point PP.

Other types of actuators 64 are also contemplated since all that is required of the actuator 64 is that it be independently activated and able to move the arms 62 to cause the respective leg 52 to pivot about ball joints 56 and 60, which thereby moves the attachment platform 32 to position the effectuator end 46 correctly. One other type of actuator contemplated is one driven by a stepper motor which does not require a resolver 66 to determine the position of the motor.

Returning to FIG. 2, the base attachment points T are shown as forming a virtual base platform 76, which is not a physical platform, but a plane which intersects the points of attachment between the actuator 64 and the ball joints 60 and is used as a reference or base in the translation section 20 of the system 5.

In the embodiment illustrated in FIG. 2, the micromanipulator 14 is shown having six legs 52 and six corresponding actuators 64. This combination was chosen to provide six degrees of freedom to the platform 32 and thereby give the surgeon six degrees of freedom for positioning the effectuator end 48. Once the microtool 44 has been constrained in the plane of the exterior wall of the biotic structure, such as by a puncture point in the sclera, the surgeon will be limited to three degrees of freedom. The surgeon utilizing a micromanipulator 14 attains an additional degree of freedom, because the effectuator end 48, such as micropipette 50, can move axially (in and out) through the needle 46 to the target within the eye. The present invention can be adapted for use with either more or less legs 52 and respective actuators 64.

The axial movement of the effectuator end 48 is performed by its own independent actuator 65, which is controlled by the plunge activation control 29, shown, for example, as a thumb-wheel or knob on the handle 24 of input device 10. Yet another available degree of freedom that can be realized with the system 5 is that of rotating the microtool 44 about its axis in a clockwise or counter-clockwise direction.

Although the legs 52 have a fixed length FL in the illustrated embodiment, since each leg 52 is independently pivotal about the ball joints 56 and 60, there is an enormous number of leg 52 position combinations available through actuators 64. Each combination translates to a unique platform 32 position that corresponds to a unique effectuator end 48 position with respect to the puncture point PP. This large number of leg 52 positioning combinations that correspond to the desired movement and location of the effectuator end 48 could not be performed by a surgeon utilizing the currently available systems for adjustments. Even the most skilled surgeon, would not be able to figure out the appropriate leg positions to arrive at the desired movement of the effectuator end 48. Therefore, the present system 5 provides the surgeon with at least six degrees of freedom (three in the illustrated embodiment of FIG. 7 when constrained by a puncture point) while the calculations and requisite leg 52 positioning remains transparent to the surgeon through the control of the computer 12.

Figure 7:
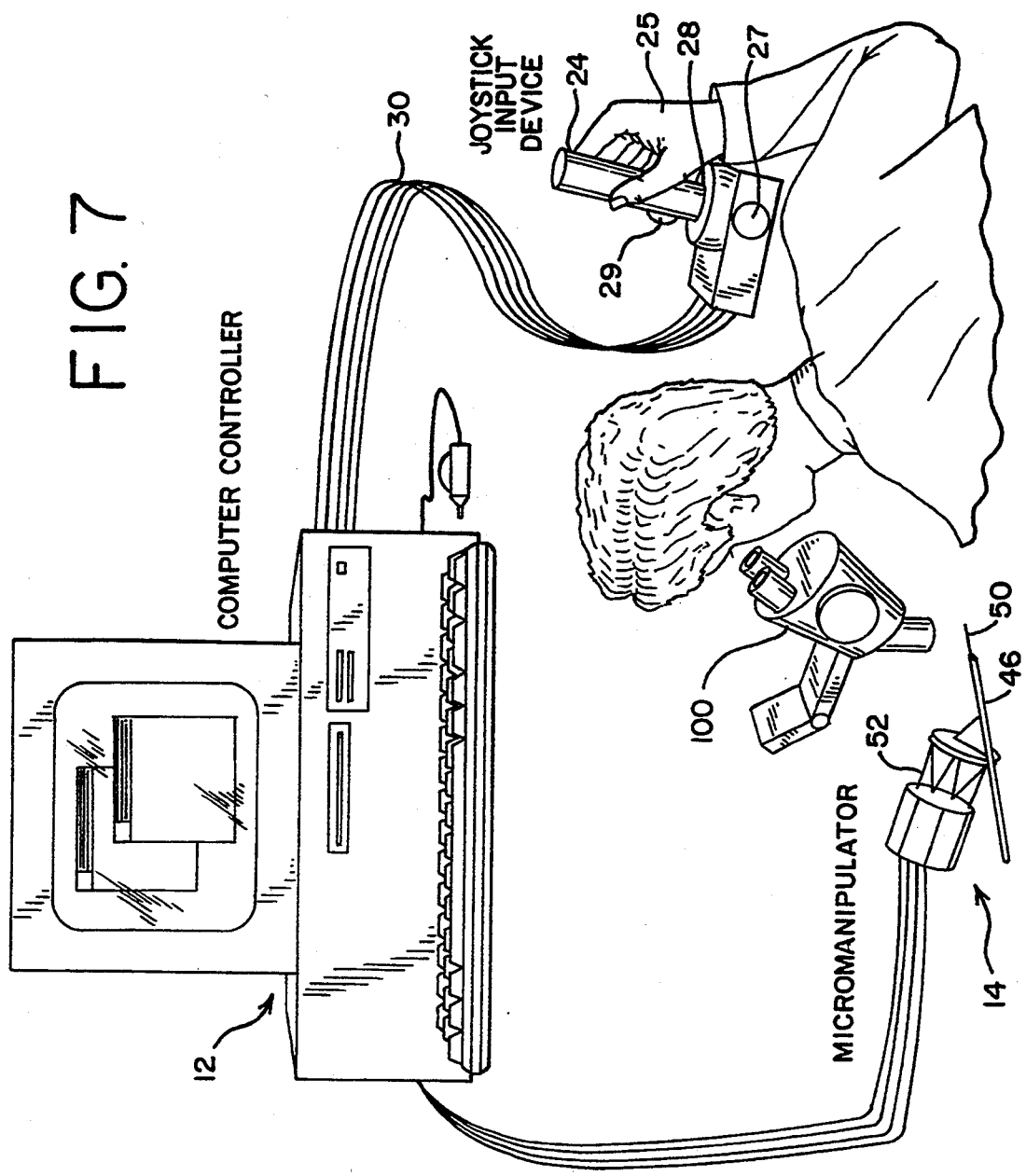
FIG. 7 depicts a graphical representation of one embodiment of a micromanipulator control system according to the invention in its contemplated use.

As shown best in FIGS. 1 and 7, the computer 12 can be any available electronic computing device, such as an industry standard architecture (ISA) IBM compatible personal computer using an Intel 486 microprocessor, adapted with an input port for coupling to the input line 30 (resolver interface, Model IBR-14-4-12V marketed by Computer Conversions Corp., 6 Dunton Court, East Northport, N.Y.) and an output port that couples to the micromanipulator 14 (e.g. a D/A converter, Model CIODAC08 marketed by Computer Boards, Inc. of 44 Wood Avenue, Mansfield, Mass.). The computer 12 includes electronic circuitry for temporary and permanent memory storage and the ability to rapidly compute fairly complicated sequences of mathematical routines in order to drive the micromanipulator 14 responsive to the surgeon's hand motions in the input device 10. It is further contemplated that the program running the system 5 can be encoded on a chip.

Figure 4:
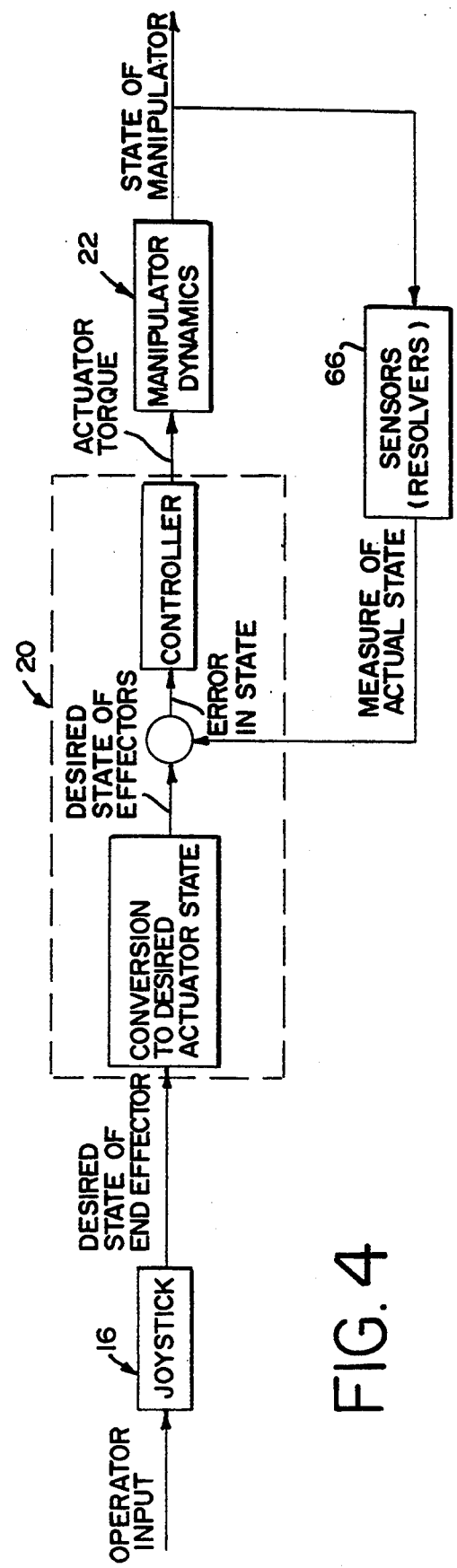
FIG. 4 depicts in detail the control system of one embodiment of the present invention.

Referring now to FIG. 4, there is illustrated a detailed diagram of the control flow of the system 5 which will be described with reference to FIGS. 1, 3 and 4. The computer 12 determines the required movement of the legs 52 to effectuate a given positioning of the effectuator end 48, by relying on the fact that every point on the needle 46 must move in a circular path with its center at the puncture point PP. In fact, every point on the platform 32 (since it is preferably rigidly attached to the needle 46) must move in a similar circular path. This is called "puncture-centered" or "spherical" movement of the microtool 44. The puncture center is the physical constraint imposed on the micromanipulator 14 or microtool 44 because of the nature of the surgery, such as in intraocular procedures, or it can be constrained by prescription based on the procedure or application.

With that in mind, once the needle 46 and effectuator end 48 have punctured the sclera, the computer 12 must take note of the surgeon's command generated by the input device 10. This command tells the computer 12 the new desired location of the effectuator end 48. Referring to the upper ball-joints 56 on the platform 32, since these ball joints 56 (platform attachment points) must move in a circle, the computer 12 must calculate what the new position of each of the legs 52 must be to generate the spherical motion necessary to give the surgeon what he has commanded via the input device 10. The process is performed for each of the six platform attachment points 37 (Q) with respect to each leg 52. The computer 12 must then determine the actuator 64 extension which will result in that platform attachment point 37 (Q) being at the correct position for each leg 52. There is only one correct value of each actuator 64 extension that will do this. The determination of actuator 64 extension is repeated for each of the six platform attachment points 37 (Q) with respect to each leg 52. Finally, once the effectuator end 48 has been positioned, this cycle begins again with any new joystick commands that may have come in while the computer 12 was calculating.

Before describing the control flow of the system 5 in more detail, the three coordinate systems used by the computer 12 will be described. The coordinate system upon which the computer 12 performs its tasks may be named the "base", "star", and "prime" coordinates. The "base" coordinate has its origin at the center of the micromanipulator 14 base (not shown) and is fixed so that it does not ever move with respect to the earth (or "ground"). The "star" (*) coordinate system is always purely translated (never rotated) from the base system. Its origin always lies at the puncture point PP. The star origin can be received as being attached by an imaginary ball joint or fulcrum to the puncture point PP, and as having its z-axis (z*) always pointing in the same direction as the base system's z-axis (z). The "prime" coordinate system has its origin always coincident with the star origin and hence with the puncture point PP also. The prime system ('), however, is fixed to the needle 46 and lies along the needle 46.

The base attachment point T, referenced to above, is a kinematic reference to the virtual parallel platform from which this mechanism was derived. As stated above, it is somewhat of a misnomer for this micromanipulator design 14, since it is not an actual point of "attachment". In the illustration shown in FIG. 2, the linear actuators 64 pass through the imaginary base at a particular point in space with respect to the base coordinate system. While it is kinematically identical, the illustrated micromanipulator 14 has no "base plate" per se. The base attachment points (T) can be defined to be anywhere along the line of travel of the linear actuators 64. The coordinates of these points have been chosen such that the actuator length (distance from base attachment point to the point where the actuators 64 are coupled to the legs 52 at lower ball joints 60) is zero at its reference state.

The reference state refers to the effectuator end 48 state achieved by translating the platform 32 a given distance. In the illustrated embodiment, one inch in the z-axis direction is preferred from the calibration state. Since one inch is ½ the full actuator 64 travel of the actuator in this illustrated embodiment, this puts each actuator 64 in the center of its range. The calibration state refers to the effectuator end 48 state achieved when all actuators 64 are fully retracted against their proximal physical stop. Z-axis (of base coordinate system) is always normal to the virtual base platform 76 and is positioned at the center of platform 76. The puncture point PP lies in the x-z plane of the base coordinate system. (See FIG. 3).

Within the input section 16, the input device 10 is a relative input device where the output ($\theta_0$, $\theta_1$, $\theta_z$) is taken by the computer 12 to be displacement from the effectuator ends 48 current state (not from any absolute reference state). The surgeon commands the micromanipulator 14 much in the same way that a pilot controls an aircraft. For example, forward and backward movement of the input device 10, such as the joystick ($\theta_0$), "pitches" the platform 32, resulting in rotation of the platform 32 and microtool 44 about the y' axis. Left and right movement of the joystick ($\theta_1$) are "yaw" inputs, yielding rotation of the platform 32 and microtool 44 about the x' axis. The surgeon can visually determine whether pitch or yaw or some combination thereof is appropriate to achieve the desired movement because the effectuator end 48 has an asymmetric geometry, since the needle 46 is placed at a 45° angle relative to the platform 32. Thus, although the surgeon gives relative commands, the composite absolute rotations and translations from the reference state are accumulated by the computer and used in the control routine.

$\theta_z$ is used to perform open loop control of the seventh actuator 65. The resulting "plunge" action advancing the micropipette 50 or other microtool 44 which is constrained by the needle 46 to move in the z' direction. This action allows the surgeon to puncture the desired vessel or perform any other function the microtool 44 is designed to perform. Since this is an open loop, there is no control or sensor reading, so the seventh actuator signal can be output at this stage of the process.

Moving now to the computer or translation section 20, the computer 12 must first determine the desired state of the effectuator end 48, (actually the movement of the actuators 64) given that the micromanipulator 14 is at any point described in the prime coordinate system by an ordered triple (x',y',z') and which can also be described with respect to the star coordinate system with a different ordered triple (x*,y*,z*). If the two coordinate triples share a common origin (as they do in this case at puncture point PP), then transformation from the prime to the star coordinates can be accomplished by multiplying the original description by an ordered series of three 3×3 matrix multiplications. Each 3×3 matrix will be called a "rotation matrix" and will be denoted by R.

Because rotation about z' is not allowed for this system, only rotation about x' and y' axes need to be considered, and therefore, the number of necessary multiplications is reduced to two. The pure rotation of matrices about x' and y' have the form:

$$Rx' = \begin{bmatrix} 1 & 0 & 0 \\ 0 & \cos(\theta_{x'}) & -\sin(\theta_{x'}) \\ 0 & \sin(\theta_{x'}) & \cos(\theta_{x'}) \end{bmatrix}$$

-continued $$R_{y'} = \begin{bmatrix} \cos(\theta_{y'}) & 0 & -\sin(\theta_{y'}) \\ 0 & 1 & 0 \\ \sin(\theta_{y'}) & 0 & \cos(\theta_{y'}) \end{bmatrix}$$

respectively, where $\theta x'$ and $\theta y'$ are the angles of rotation from star to prime. A point in the prime coordinate system is represented as a column vector:

$$P' = \begin{bmatrix} x' \\ y' \\ z' \end{bmatrix},$$

and the prime coordinate system is rotated $\theta x'$ and $\theta y'$ from the star coordinates, then P* will be the column vector corresponding to the point in the star system and is given by:

$$P^* = \begin{bmatrix} \cos(\theta_{y'}) & 0 & -\sin(\theta_{y'}) \\ 0 & 1 & 0 \\ \sin(\theta_{y'}) & 0 & \cos(\theta_{y'}) \end{bmatrix} * \begin{bmatrix} 1 & 0 & 0 \\ 0 & \cos(\theta_{x'}) & -\sin(\theta_{x'}) \\ 0 & \sin(\theta_{x'}) & \cos(\theta_{x'}) \end{bmatrix} *_{P'}$$

In this way, the coordinates of the leg attachment points "Q" along the upper ball joints 56, which are fixed in the prime system, can be translated into the star system if the absolute rotations from the reference state are known. Then, from the star system it is a simple origin translation to get the description of the attachment points Q with respect to the base coordinate system (e.g. In the illustrated embodiment, $T_{bp}$=(0.8, 0, 4.191) where $T_{bp}$ is the translation from the star origin to the base origin).

Note that by defining the star coordinate system to be in pure translation from the base coordinate system and in pure rotation from the prime coordinate system, the mapping from prime to base is easily broken down into two simple steps. First, rotate the coordinates from the prime system to the star system. Second, translate the coordinates from the star system to the base system. Also, by defining the prime and star coordinate system origins to be at the puncture point PP (about which pure rotation of the platform 32 is desired) the mathematics of imposing the kinematic constraint of pure rotation becomes trivial in contrast, for example, to choosing the tip of the micropipette 50 to be the prime origin.

Further, the coordinates of the base attachment points are fixed in the base coordinate system. Once the platform attachment points (i.e. the Q coordinates) with respect to the base coordinate system are known, then the vectors which represent the point connecting each base attachment point T to its corresponding platform attachment point Q are obtained by simple vector subtractions. These resulting vectors are defined as virtual legs VL. The length of each virtual leg VL defines a unique configuration of the legs 52 in terms of position and actuator 64 extension. The actuator extension is obtained by solving the geometry of a triangle whose sides are the virtual leg VL, the leg 52 having length FL, and the vertical length of the actuator 64 from base attachment point T to the lower ball joint 60 center, which is a known value. (See FIG. 3).

Next, since the actuators 64 are actually rotary electric motors 68 with rotary to linear transmissions (ballscrews 72) attached, the desired extension or retraction must be converted (by a constant multiplier determined by the dimensions of the actuator 64) to the desired rotary position of the motors 68. Once the desired rotary positions $K_p$ are known, the desired angular velocity $K_v$ or torque can be approximated by the difference between the previous value and the current value of the desired rotary position divided by the time taken for one pass through the cycle of the system 5. At this point the desired state has been determined completely and the desired motor position and velocity are ready for comparison to measured values. Next the computer 12 estimates the actual state of the actuators 64, which is simply the operation of reading the micromanipulator's sensors, resolvers 66 to obtain a measure of actual motor position for comparison with the desired state.

Once the actual state has been estimated, then the computer 12 takes the measured rotary position and angular velocity of the actuators 64 which is subtracted from the desired rotary position to yield the error in rotary position and velocity. The desired motor torque is then a linear combination of these two errors (for each of the six actuators 64). Finally, each desired motor torque is multiplied by a given constant, which is determined by the type of motor selected and the desired torque for that motor, to convert it to an appropriate command voltage that is output from the computer 12 to a corresponding analog motor amplifier 69. The voltage command is converted by the amplifier to a winding current which will produce the desired torque to the motors 68 and thereby extend each of the actuator arms 62 causing the respective leg 52 to pivot at points Q and T, the proper amount to effectuate the movement of the platform 32 and the corresponding position of the microtool 44, all based upon the surgeon's hand movement on the input device 10.

Referring now to FIG. 5, there is shown a more detailed diagram of the control flow of one embodiment of the system 5 occurring during each movement of the input device 10 by the surgeon's hand. Initially, the attachment points $Q_N$, where N is the number of legs, must be initialized or set. $A_{p'}$ is a 3×6 array, each column of which is a vector from the origin of the prime coordinate system to one of the six platform attachment points $Q_N$ on the platform 32 to which a leg 52 attaches together with the upper ball joints 56. $A_p$ is a similar array describing the same six points $Q_N$ but with respect to the base coordinate system. $A_b$ is and array which describes of the base attachment points $T_N$ with respect to the base coordinate system. Next, the computer 12 must initialize a composite rotator matrix $T_{bp}$, where $T_{bp}$ is the translation vector from the base coordinate origin to the prime/star coordinate origin. The "bp" subscript mnemonic is "from base to puncture point". At this point the constant $L_{fl}$ is also set. The constant $L_{fl}$ is the physical length of each leg 52 (2 inches in the illustrated embodiment of the fixed-leg platform configuration).

Following the initialization, the input device 10, typically the joystick, is read by the computer 12 where $\beta=(\theta_0,\theta_1,\theta_z,\theta_s)$ is the numeric representation of the electronic signal caused by moving the joystick. Then, the two (3×3) rotation matrices $R_{\theta 0}$ and $R_{\theta 1}$ are formulated, and any sensitivity input from the joystick is implemented. $\theta_s$ is a sensitivity parameter used to modify gains $J_{\theta 0}$ and $J_{\theta 1}$ which in turn are used to transform $\theta_0, \theta_1$ to radians of needle tilt. Based on this, a seventh actuator 65 is moved appropriately where $\theta_z$ is multiplied by a predetermined constant selected to provide the desired actuator gain and then output to the actuate actuator 65 and thereby "plunge" the tip of the microtool 44, such as micropipette 50. The plunge action is controlled by the surgeon using the plunge activation control 29. The computer 12 then awaits another input from input device 10.

Thereafter, the conversion block 82, of system 5 is entered, where the computer 12 performs the calculations that will be used to activate the actuators 64 to obtain the desired movement in legs 52, which the surgeon sees as the positioning of microtool 44. Accordingly, the computer 12 formulates the rotation matrices which will transform the platform attachment points $Q_N$ to the star coordinate description $Q_{N*}$. The relative rotation must also be changed into an absolute rotation from the reference. Here the variable $R_c (3 \times 3)$ is the composite of all past rotations. $R_t$ is the total rotation matrix $(3 \times 3)$ to be calculated. To rotate about a previously rotated frame, a postmultiplication is performed, where $R_t = R_c * R_{\theta 0} * R_{\theta 1}$.

Next, within the conversion block 82, the computer 12 transforms the set of platform attachment points $Q_N$, by retrieving $A_p'$, the $(3 \times 6)$ matrix of platform attachment points $Q_{N'}$, from memory. It then rotates that array by $R_t$ to get the description of the points $Q_N$ in the star coordinate system, and translate the origin by $T_{bp}$ to get the description in the base coordinate system. Accordingly, $A_p = R_t A_p' + T_{bp}$. Then, to keep the system 5 current, a history or composite matrix $R_c$ must be updated and $R_t$ will be the composite rotation matrix next time through the loop so $R_c = R_t$.

Following the transformation routine, the computer 12 must find the vectors representing the virtual legs VL in order to determine how the actuators 64 will move the actual legs 52. The system 5 does this by retrieving $A_b$, the $(3 \times 6)$ matrix of base attachment points (with respect to base system) from memory. It then must calculate the matrix $L_v (3 \times 6)$, the virtual leg vectors ("virtual" because these vectors have their heads at the platform attachments Q and tails at the base attachments T and would correspond to the actual legs if this were a pure Stewart type platform). Each column of $L_v$ is a virtual leg vector, where $L_v = A_p - A_b$. Then, the desired actuator 64 extension must be determined. The constant $L_{fl}$ and the length FL of each leg 52 is retrieved and used in conjunction with the columns of $L_v$, $(L_1, L_2, \ldots L_6)$ to calculate the actuator extensions $E_i$, where $E_i = L_{iz} - ([L_{fl}^2 - (L_{ix}^2 + L_{iy}^2)])^{\frac{1}{2}}$ for $i = 1 \ldots 6$.

All the above calculations are performed before any actual physical movement of actuators 64 has been performed, since the computer 12 must convert the linear values to rotary displacement values, as illustrated in block 90. First, the computer 12 converts the linear displacement $E_i$ to rotary displacement $(X_d)$ necessary for the proper activation of the motor 68 and ballscrew 72 to extend the actuator arm 62 properly. This gives the desired mechanical position in a "number of turns" value. Thus, $X_d = E_i / \text{Pitch} + \text{Offset}$, where Offset is the number of turns from calibration to reference. Then, the computer 12 differentiates $X_d$ to get the desired velocity, represented at 92. The result will be an approximation to the true continuous derivative of the desired position. There are many possible methods of arriving at such an approximation, but a simple method is presented here for illustrative purposes. $V_d = (X_d - X_{dlast}) / (\text{Cycle Period})$, where the cycle period is the time between samples of position, and $X_{dlast}$ is the previous desired position (i.e., the previous cycle's $X_d$). Finally, Update $X_{dlast}$ is updated in preparation for the next cycle, where $X_{dlast} = X_d$. The computer then must read resolvers 66 in order to obtain an estimate of the actual position $(X_a)$ and to obtain an estimate of the actual velocity $(V_a)$.

The values of $X_a$ and $V_a$ are critical in determining the proper extension of the actuator arms 62 by actuators 64 to achieve the precision of movement required of the microtool 44. In the controller block 94, the computer 12 calculates the error in position where, $X_{error} = X_d - X_a$, and calculates the error in velocity, represented as $V_{error} = V_d - V_a$. Together these values, $X_{error}$ and $V_{error}$ are used to determine the correct extension of the actuator 64 from its last position. With these values now known, the computer 12 must calculate the error-correcting torque that is to be applied to the actuators 64 to obtain the surgeon's desired position of the microtool 44. As with the digital differentiation, there are many possible control laws that may be employed to find the desired torque. A simple and robust one is given as an example. It has been found that $\text{torque}_d = K_p (X_{error}) + K_d (V_{error})$, where $K_p$ and $K_d$ are proportional and derivative gains, respectively (e.g. In the illustrated embodiment $K_p = 10$ and $K_v$ will be 0.1). There are also gains for converting from torque to rotor current and then to a voltage command to a motor amplifier to achieve the desired rotor current, where $\text{Volt}_{command} = (\text{Torque}_d)(K_{motor})(K_{amp})$. When this $\text{Volt}_{command}$ is generated from a D/A converter output of the computer 12 to the amp (not shown), the motor 68 will act as a torque source at the "Torque$_d$" level.

A computer program written in the language C to implement the illustrated embodiment of FIG. 5 is provided in Appendix A.

The manipulator dynamics block 96 represents the resulting behavior of the micromanipulator 14 device after the desired torque Torque$_d$ is applied. There is no computer 12 functioning associated with this block. Once the actuators 64 have been torqued and the resulting leg 52 movement, platform 32 movement and desired microtool 44 positioning has been accomplished, the system cycle is begun again.

Figure 6:
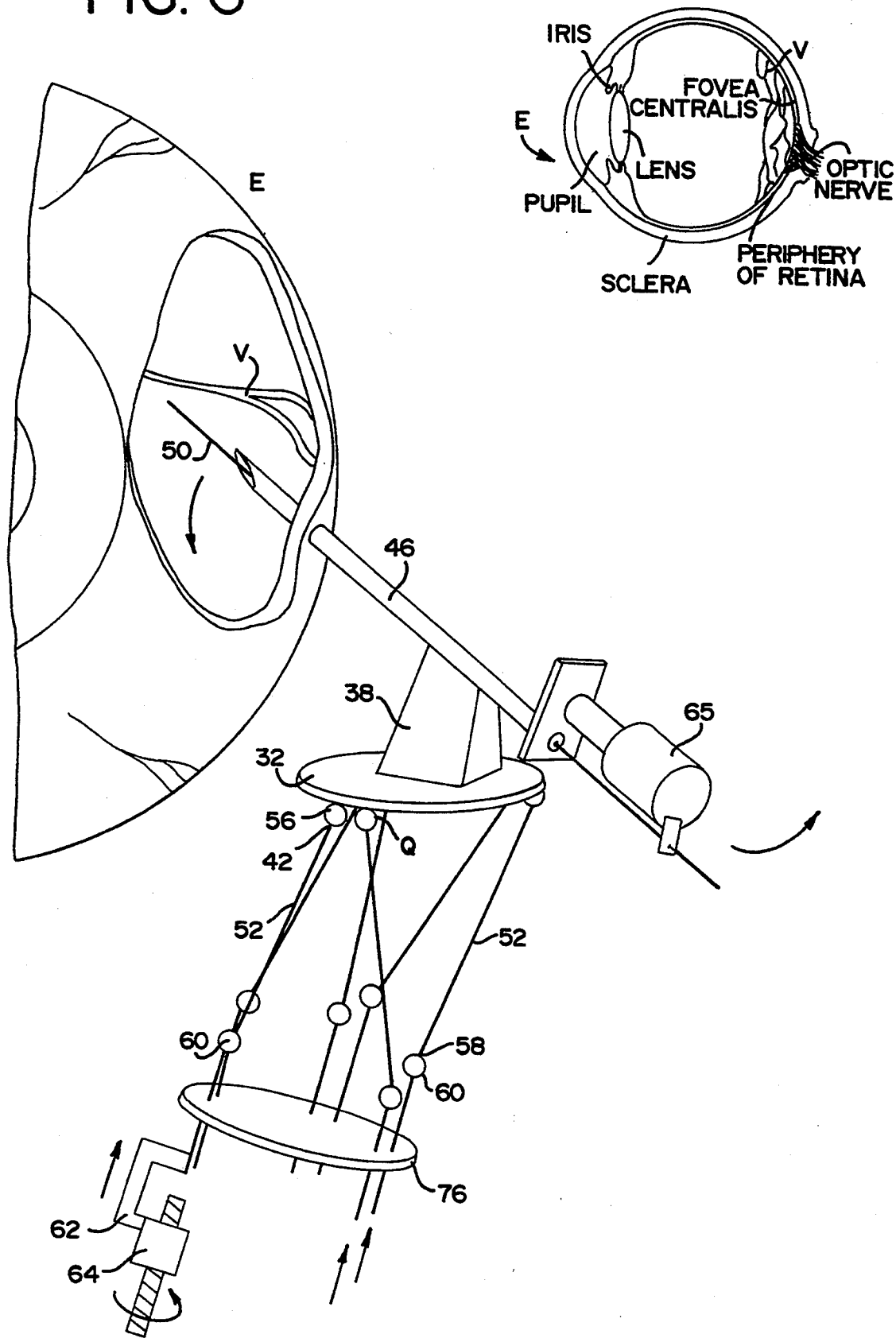
FIG. 6 depicts one embodiment of the present invention in use during optical vascular surgery and a human eye for reference.

In operation, referring now to FIGS. 6 and 7, the surgeon will typically be viewing the microtool 44 with the patient's eye through a microscope 100 focusing through the pupil of the eye E. Utilizing the joystick, the surgeon can drive the microtool 44, such as needle 46, to the desired location with respect to a given vessel. As the surgeon moves the handle 24, his hand motions are translated by the computer 12 using the above described control loop of the system 5, and replicated through the micromanipulator 14 to position the needle 46 where directed by the surgeon.

The computations and calculations defined above should happen virtually instantaneously with the surgeon's hand motion on the joystick to create the illusion that the microtool 44 is an extension of the surgeon's hand. The advantage of the present system 5 is that the surgeon sees the microtool 44 move in synchronicity with his hand motions. Once the needle 46 is properly positioned, the surgeon, using the additional degree of freedom given by actuator 65, can actuate the plunge action of the micropipette 50 to puncture the vessel V and deliver the given drug thereto.

Referring specifically to FIG. 6, the eye E is shown with the micropipette 50 having been actuated towards the vessel V going through the needle 46. A graphical representation of the top of the micromanipulator 14 is shown guiding and positioning the needle 46. If the surgeon (looking through the microscope 100) sees that the micropipette 50 needs to go down (see the arrow in the figure), he will push forward on the joystick (like making the nose of a plane go down in a video game using a video game joystick controller). The computer 12 working behind the scenes makes that happen. But the computer 12 only has control over the six motors 68, which move the six linear sliders 74 down below the "base". One motor/slider combination has been referred to here as an actuator 64. So the computer 12 determines how to move the six actuators 64 to give the surgeon the movement requested through the input device 10 consistent with the desired predetermined constraints (i.e. the constraint of translation or rotation about the puncture point PP through the sclera).

The present invention not only provides the surgeon with a simple to use micromanipulator system, but also gives the surgeon great flexibility and speed, while increasing precision by eliminating human error in moving the microtool 44 when constrained to three degrees of freedom by a puncture point or other fixed point. The present system 5 can be easily transported and its size and configuration allows the surgeon to use several of the systems 5 in surgical procedures demanding more than one micromanipulator 14. Also, the present invention, including the micromanipulator 14, actuators 64, and microtool 44, can be configured to fit into a volume roughly similar to the volume taken up by a surgeon's hand holding an instrument.

The system 5 will give the surgeon a level of control far beyond what is currently available. Using the present invention, procedures such as introducing clot dissolving drugs into the retinal vessels near the location of the clots can be performed efficiently, quickly and with less trauma to the eye. Various other retinal microsurgical techniques are also envisioned.

One example where this technique may be particularly helpful is in retinal vascular obstruction, where blood clots lodge in the vessels and impede the flow of blood. Using the present computer assisted micromanipulation control 5, clot dissolving drugs can be introduced directly to the retinal vessels V near the location of the clots. Current treatment for retinal vascular obstructions are very limited. Moreover, various other retinal microsurgical techniques are also envisioned and the use of the present computer control system 5 can be directed to other areas of surgery, such as neurosurgery, which utilize micromanipulation or even other surgical techniques where micromanipulation is not a factor.

Finally, it must be understood that the present system 5 allows the micromanipulator 14 to have at least six degrees of positioning freedom (the axial movement of the micropipette 50 will also add a seventh degree of freedom for the system) when not constrained at a point. The flexibility provided by the freedom of movement permits the micromanipulator 14 to be adapted for use in a limitless number of applications (e.g. non-medical applications, such as robotics, where the micromanipulator 14 could be adapted as a wrist for a robot in industrial uses). Further, it is envisioned that the present micromanipulator 14 and system 5 could be configured for use in a master-slave system where a micromanipulator 14 is a component, or slave, to a master micromanipulator.

While embodiments of the present invention have been shown and described, it will be appreciated by those in the art that changes and modifications may be made thereto without departing from the invention in its broader aspects and as set forth in the following claims.

```
/*
****************************************************************
**********************************************************
***                                              **********
***   C O N T R O L . C                          **********
***                                              **********
***   Pat Jensen                                 **********
***   Biomedical Engineering                     **********
***   Northwestern University                    **********
***                                              **********
***   March 20, 1993                             **********
***                                              **********
****************************************************************
****************************************************************

This file contains the control loop for running the
    robot. It is interrupt driven to acquire, calculate,
    and set the motor torques to obtain a desired motion
    profile.

*/

/* Included files */
#include <stdio.h>
#include "robot.h"
#include "control.h"
#include "debug.h"
#include "adc\adc.h"
#include "resolver\resolver.h"
#include "encoder\encoder.h"
#include "dac\dac.h"
#include "move.h"
#include "pid.h"

/*
```

```
/*****************************************************************
*** C o n t r o l L o o p ( )                    **********
*****************************************************************
    This function handles the needed overhead for control
    every x milliseconds.  The interrupt is generated by the
    ADC card on a periodic basis.
*/
void ControlLoop ( RobotMove *robotMove, RobotControl *robotControl )
{
    int i;

/* Kill the motors and return on any pending error !!! */
    if ( robotError )
    {
        for ( i=0; i<NUM_JOINTS; i++ )
            robotControl->motorOutput[i]=0.0;
        RobotWriteDAC ( robotControl );
        return;
    }

/* Read Strain Gauges, Joystick Sensitivity, and Digital I/O */
    if ( !RobotReadADC(robotControl) )
    {
        robotError = ERROR_ADC;
        return;
    }

/* Check for EM Stop */
    if ( !robotControl->powerEnable )
    {
        robotError = ERROR_EMSTOP;
        return;
    }

/* Read Motor Position */
    if ( !RobotReadResolver(robotControl) )
    {
        robotError = ERROR_RESOLVER;
        return;
    }

/* Read Encoder Position */
    if ( !ReadEncoder(robotControl) )
    {
        robotError = ERROR_ENCODER;
        return;
    }

/* Calculate the new robot position */
    switch ( robotControl->moveType )
    {
        /* Move along a Bang-Bang profile */
        case MOVE_BANG_BANG:
            if ( !BangBangMove(robotMove,robotControl) )
            {
                robotError = ERROR_MOVE;
                return;
            }
            break;

/* Use the joystick as movement input */
        case MOVE_JOYSTICK:
            if ( !JoystickMove(robotControl) )
            {
                robotError = ERROR_MOVE;
                return;
            }
            break;

/* Use a file as joystick input */
        case MOVE_JOYSTICK_FILE:
            if ( UpdateJoystickFromFile(robotControl) )
            {
                if ( !JoystickMove(robotControl) )
                {
                    robotError = ERROR_MOVE;
                    return;
                }
            }
            break;
```

```c
        /* Set the desired position equal to the actual for tracking */
        case MOVE_FREE:
            if ( !FreeMove(robotControl) )
            {
                robotError = ERROR_MOVE;
                return;
            }
            break;

/* Keep the same desired position as last time */
        case MOVE_FIXED:
        default:
            break;
    }

/* Calculate the new motor tourques */
        if ( !PID(robotControl) )
        {
            robotError = ERROR_PID;
            return;
        }

/* Set the motor output */
        if ( !RobotWriteDAC(robotControl) )
        {
            robotError = ERROR_DAC;
            return;
        }
} int ReadEncoder(RobotControl *robotControl)
{
    robotControl->joyX = 0.0;
    robotControl->joyY = 0.0;
    robotControl->joySense = 1.0;
    robotControl->joyOn = TRUE;

return(TRUE);
}

/*
***************************************************************
***************************************************************
***                                            **********
***  D E B U G . C                             **********
***                                            **********
***  Pat Jensen                                **********
***  Biomedical Engineering                    **********
***  Northwestern University                   **********
***                                            **********
***  March 20, 1993                            **********
***                                            **********
***************************************************************
***************************************************************

This file contains a collection of routines designed to
    aid in the debugging of the system.  If debugging is
    desired, the #define DEBUG statement in ROBOT.H needs to
    be uncommented.

*/

/* Included files */
#include <stdio.h>
#include <stdlib.h>
#include "robot.h"
#include "qwindow\qwindow.h"
#include "debug.h"

/* Variables that are global only to this file */
#define DEBUG_LENGTH    50
double debugArray1[DEBUG_LENGTH];
double debugArray2[DEBUG_LENGTH];
double debugArray3[DEBUG_LENGTH];
double debugArray4[DEBUG_LENGTH];
double debugArray5[DEBUG_LENGTH];
double debugArray6[DEBUG_LENGTH];
int debugIndex=0;

/*
***************************************************************
***  D e b u g C o l l e c t D a t a           **********
***************************************************************
```

```
     This function stores data into debug arrays as programmed.
     It should be noted that this program violates the philosophy
     used throughout the rest of the program because it must access
     the robotControl structure directly instead of via a pointer.

*/
void DebugCollectData (double a, double b, double c, double d, double e, double f)
{
    if ( debugIndex>=DEBUG_LENGTH-5)
    {
        robotError=ERROR_DEBUG;
        return;
    }
    debugArray1[debugIndex] = a;
    debugArray2[debugIndex] = b;
    debugArray3[debugIndex] = c;
    debugArray4[debugIndex] = d;
    debugArray5[debugIndex] = e;
    debugArray6[debugIndex] = f;
    debugIndex++;
}

/*
***************************************************************
*** D e b u g P r i n t D a t a ( )              **********
***************************************************************

This function prints the debug information to the screen.
    Both this and the DebugCollectData() function are shells
    that are to be filled in as necessary to acquire the desired
    data.

*/
void DebugPrintData ()
{
    int i;

printf ( "Printing the debug info\n" );
    for ( i=0; i<DEBUG_LENGTH; i++ )
        printf ( "%lf, %lf, %lf, %lf, %lf, %lf\n",
                 debugArray1[i], debugArray2[i], debugArray3[i],
                 debugArray4[i], debugArray5[i], debugArray6[i] );
}

/*
***************************************************************
*** D e b u g E n t e r P I D P a r a m s ( )     *******
***************************************************************

This function provides the user with a text entry window
    for loading the PID parameters.

Passed Parameters:
        double *Kp              - Proportional Gain
        double *Ki              - Integral Gain
        double *Kd              - Differential Gain Return Value:
        none

*/
int DebugEnterPIDParams ( double *Kp, double *Ki, double *Kd )
{
    WINDOW *win;
    char KpStr[64], KiStr[64], KdStr[64], temp[255];

sprintf ( KpStr, "%.3lf", *Kp );
    sprintf ( KiStr, "%.3lf", *Ki );
    sprintf ( KdStr, "%.3lf", *Kd );

if ( (win=establish_window(15,8,7,40)) != NULL)
    {
        set_colors(win,ALL,BLUE,WHITE,BRIGHT);
        set_title(win, " PID Control Gains ");
        display_window(win);
        establish_field(win,2,1," Kp: _____ (mNm/rad)", KpStr, 'A' );
        establish_field(win,2,2," Ki: _____ (mNm*sec/rad)", KiStr, 'A' );
        establish_field(win,2,3," Kd: _____ (mNm*sec^2/rad)", KdStr, 'A' );
        data_entry(win);
        delete_window(win);
        if ( !sscanf(KpStr,"%lf",Kp) ) return(FALSE);
```

```
        if ( !sscanf(KiStr,"%lf",Ki) ) return(FALSE);
        if ( !sscanf(KdStr,"%lf",Kd) ) return(FALSE);
        sprintf ( temp, "Kp=%.3lf, Ki=%.3lf, Kd=%.3lf : OK (y/n) ?",
                    *Kp, *Ki, *Kd );
        if ( RobotYesNoWin(temp) )

return (TRUE);
            }
        return (FALSE);
    }

/*
***************************************************************
***************************************************************
***                                                 **********
***   M A I N . C                                   **********
***                                                 **********
***   Pat Jensen                                    **********
***   Biomedical Engineering                        **********
***   Northwestern University                       **********
***                                                 **********
***   March 20, 1993                                **********
***                                                 **********
***************************************************************
***************************************************************

This file contains the starting point of the robot
    control program.  It initializes the needed structures
    and provides a simple user interface.

*/

/* Included system files */
#include <stdio.h>
#include <stdlib.h>
#include <sys\timeb.h>
#include <dos.h>

/* Included program files */
#define ROBOT_MAIN
#include "robot.h"
#include "debug.h"
#include "control.h"
#include "adc\adc.h"
#include "resolver\resolver.h"
#include "encoder\encoder.h"
#include "dac\dac.h"
#include "move.h"
#include "pid.h"
#include "int.h"
#include "menu.h"

/* Local prototype definitions */
void main ();

/*
***************************************************************
*** M A I N ( )                                     **********
***************************************************************

This is the main starting point of the program.
    It starts the interrupt generator located on the
    A/D card for 1KHz and then calls the menu function.
    The menu is event driven an takes no processor time
    when idle.  The control loop runs continuously in the
    background until the program is exited.

*/
void main ()
{
    /* Initialize the control variables to default values */
    RobotSetControlParams ( &robotControl,
                            DEFAULT_KP,
                            DEFAULT_KD,
                            DEFAULT_VEL_BW);

/* Initialize the system */
    robotError = RobotInit(&robotControl,&robotMove);

/* Start the event driven menu */
    RobotMenu ();
```

```
    /* Initialize the system */
    robotError = RobotInit(&robotControl,&robotMove);

/* Print out the debug information */
#ifdef DEBUG
    DebugPrintData ();
endif DEBUG exit ( robotError );
}

/*
****************************************************************
****************************************************************
***                                                  **********
***  M E N U . C                                     **********
***                                                  **********
***  Pat Jensen                                      **********
***  Biomedical Engineering                          **********
***  Northwestern University                         **********
***                                                  **********
***  March 20, 1993                                  **********
***                                                  **********
****************************************************************
****************************************************************

This file contains the routines for operating the event
    driven user interface. The user interface was adapted
    from Al Steven's book "Quick C". It is a simple to use,
    low overhead, text based user interface. All the routines
    called from the interface are located below.

*/ define MENU_C
include <stdio.h>
#include <stdlib.h>
#include <dos.h>
#include "robot.h"
#include "qwindow\qwindow.h"
#include "qwindow\keys.h"
#include "menu.h"

/*
****************************************************************
*** R o b o t M e n u ( )                            **********
****************************************************************

This function initializes the menu and loads the menu
    functions for future calling.

Passed Parameters:
        none

Return Value:
        none

*/
void RobotMenu ()
{
    /* Create the background window */
    if ( (backwind=establish_window(0,0,25,80)) != NULL)
    {
        /* Load the error handler with robot functions */
        set_error_handler ( &robotError, RobotErrorHandler );
        set_colors(backwind,ALL,BLACK,WHITE,DIM);
        set_colors(backwind,ACCENT,GREEN,BLACK,BRIGHT);
        set_colors(backwind,NORMAL,BLACK,GREEN,BRIGHT);
        set_title(backwind, " Win Test ");
        display_window(backwind);
        /* Start the menu */
        menu_select(" Micromanipulator Menu ", &menu[0]);
        close_all();
    }

/*    fn_index = 0;
    set_fnbar (fn_str[fn_index]);*/
}

/*
```

```
/*
***************************************************************
*** RobotErrorHandler( )                     **********
***************************************************************

This function handles any robot errors that occur.  In
    the control loop (called every millisecond from an A/D
    interrupt), a variable robotError is set to one of several
    values if an error occurs.  This variable is checked in
    the qwindow library during idle time.  If it is ever non
    zero, this function will be called.  The error flag and
    handler function were passed to the window library by a
    call to set_error_handler() above.

It currently kills the robot on ANY error.  Another
    calibration must be performed before the robot can be
    run again once an erroroccurs.

Passed Parameters:
        none

Return Value:
        none

*/
void RobotErrorHandler ()
{
    int error;
    error=robotError;
    RobotMenuPowerOff ();
    RobotErrorMessage ( errorString[error] );
}

/*
***************************************************************
*** RobotMenuPowerOn( )                     **********
***************************************************************

This function gracefully turns on power to the robot.
    It initializes the hardware, powers on the amplifiers,
    homes the robot, and then moves the robot to the center.

Passed Parameters:
        none

Return Value:
        none

*/
void RobotMenuPowerOn ()
{
    /* Ask before recalibrating if power is already on */
    if ( robotControl.calibrated )
        if ( !RobotYesNoWin("Recalibrate the robot ? (y/n)") )
            return;

/* Turn off (initialize) all hardware */
    robotError = RobotInit(&robotControl,&robotMove);
    robotControl.calibrated = FALSE;

/* Prompt operator to make sure robot is retracted */
    if ( !RobotYesNoWin("Is robot fully retracted (y/n) ?") )

{
        RobotErrorMessage ( "Please fully retract robot and PowerOn again" );
        return;
    }

/* Turn the amplifier power on */
    RobotPower ( &robotControl, 1 );

/* Load the interrupt handler which calls the control loop (see INT.C) */
    LoadIntHandler ();

/* Start the pacer clock on the A/D card which generates interrupts */
    RobotStartPacer ();

/* Perform the calibration */
    RobotErrorMessage ("Warning! The robot will move to reference position.");
    disable ();
    if ( RobotMoveReference(&robotControl,&robotMove) )
        robotControl.moveType = MOVE_BANG_BANG;
```

```
    else
    {
        enable ();
        RobotErrorMessage ( "Error in calibration routine" );
    }
    enable ();
    robotControl.calibrated = TRUE;
}

/*
****************************************************************
*** R o b o t M e n u P o w e r O f f ( )      **********
****************************************************************

This function gracefully turns off the power to the
    robot. It also has the ability to move the motors to
    the home position if this routine wasn't entered under
    duress.

Passed Parameters:
        none

Return Value:
        none

*/
void RobotMenuPowerOff ()
{
    /* Home the robot if no robot error */
    if ( !robotError )
    {
        RobotErrorMessage("Warning ! Robot will move to calibration position." );
        disable ();
        if ( RobotMoveCalibration(&robotControl,&robotMove) )
            robotControl.moveType = MOVE_BANG_BANG;
        else
        {
            enable ();
            RobotErrorMessage ( "Error in calibrate routine" );
        }
        enable ();

while(robotControl.moveType == MOVE_BANG_BANG)
            delay(100);
    }

/* Turn the amplifier power off */
    RobotPower ( &robotControl, 0 );

/* Turn off (initialize) all hardware */
    robotError = RobotInit(&robotControl,&robotMove);

/* Stop the pacer clock */
    RobotStopPacer ();

/* Restore the original interrupt vector */
    RestoreIntHandler ();

/* Clear the calibrated flag */
    robotControl.calibrated = FALSE;
}

/*
****************************************************************
*** R o b o t A b o r t ( )      **********
****************************************************************

This function performs the software equivalent of pressing
    the emergency stop button. The system is immediately powered
    down and must be recalibrated before operation can resume.

Passed Parameters:
        none

Return Value:
        none

*/
void RobotAbort ()
{
```

```
    robotError = ERROR_EMSTOP;
}

/*
***************************************************************
*** R o b o t E r r o r M e s s a g e ( )      **********
***************************************************************

This function displays an error message to the screen
    and waits for the operator to press a key.

Passed Parameters:
        none

Return Value:
        int             - TRUE for yes, FALSE for no

*/
void RobotErrorMessage ( char *msg )
{
    error_message ( msg );
    getch ();
    clear_message ();
}

/*
***************************************************************
*** R o b o t Y e s N o W i n ( )              **********
***************************************************************

This function returns TRUE or FALSE depending on the
    users response to a yes/no question.

Passed Parameters:
        none

Return Value:
        none

*/
int RobotYesNoWin ( char *s )
{
    int ch;

WINDOW *win;
    win = establish_window((80-strlen(s)-6)/2,10,3,max(10,strlen(s)+6));
    set_colors(win, ALL, GREEN, WHITE, BRIGHT);
    set_title(win, " User Input ");
    display_window (win);
    wprintf(win, "  %s", s);
    ch = get_char();
    delete_window (win);
    if ( toupper(ch) == 'Y' )
        return(TRUE);
    return(FALSE);
}

/*
***************************************************************
*** M o v e M e n u ( )                        **********
***************************************************************

This function is called from the user interface when
    a change of the type of motion is requested.

Passed Parameters:
        int     hs      - horizontal selection
        int     vs      - vertical selection Return Value:
        none

*/
void MoveMenu ( int hs, int vs )
{
    double time, pos, tacc;
    char moveFilePath[255], temp[16];
```

```
char str[255];
int i;

/* Make sure the robot is on before moving it */
if ( !robotControl.calibrated )
{
    RobotErrorMessage ( "Robot is not calibrated - please Power On" );
    return;
}

/* Stop any pending motion */
disable ();
RobotFreeze ( &robotControl );
robotControl.moveType=MOVE_FIXED;
enable ();

/* Switch on the type of move to perform */
switch ( vs )
{
    /* Actively stay at the current position */
    case MOVE_FIXED:
        disable ();
        RobotFreeze ( &robotControl );
        robotControl.moveType=MOVE_FIXED;
        enable ();
        break;

/* Apply zero torque but keep track of position */
    case MOVE_FREE:
        disable ();
        robotControl.moveType=MOVE_FREE;
        enable ();
        break;

/* Move according to joystick input */
    case MOVE_JOYSTICK:
        disable ();
        robotControl.moveType=MOVE_JOYSTICK;
        enable ();
        break;

/* Move according to joystick input read from a file */
    case MOVE_JOYSTICK_FILE:
        temp[0] = 0;
        if ( get_file_selection (MOVE_FILE_MASK,
              temp,
              FILE_SELECT,
              "Movement Profile Selection",
              "Please select from the following movement profiles") != -1)
        {
            sprintf ( moveFilePath, "%s\\%s", MOVE_FILE_PATH, temp );
            if ( ReadJoystickFile(&robotControl,moveFilePath) )
            {
                if ( RobotYesNoWin("OK to start the move (y/n) ?") )
                {
                    disable ();
                    RobotInitResolvers ( &robotControl, 0.0 );
                    robotControl.moveType=MOVE_JOYSTICK_FILE;
                    enable ();
                }
                else
                    RobotErrorMessage ( "Move aborted" );
            }
            else
                RobotErrorMessage ( "Error reading move file" );
        }
        break;

/* Perform simultaneous bang-bang move */
    case MOVE_BANG_BANG:
        pos=time=tacc=0.0;
        if ( MenuEnterBangBangParams(&pos,&time,&tacc) )
        {
            disable ();
            if ( RobotLoadBangBangMove(&robotControl,
                                       &robotMove,
                                       pos,time,tacc) )
                robotControl.moveType = MOVE_BANG_BANG;
            else
            {
                enable ();
                RobotErrorMessage ( "Entered values out of range" );
```

```
            }
            enable ();
        }
        else
            RobotErrorMessage ( "Must enter numbers" );
        break;
    }
}

/*
***************************************************************
*** D e b u g M e n u ( )                        **********
***************************************************************

This function is called from the user interface when
    a debug procedure is requested.

Passed Parameters:
        int     hs      - horizontal selection
        int     vs      - vertical selection Return Value:
        none

*/
void DebugMenu ( int hs, int vs )
{
    double Kp, Ki, Kd;

switch ( vs )
    {
        case DEBUG_PID:
            Kp = robotControl.Kp;
            Ki = robotControl.Ki;
            Kd = robotControl.Kd;
            if ( DebugEnterPIDParams(&Kp,&Ki,&Kd) )
            {
                disable ();
                robotControl.Kp = Kp;
                robotControl.Ki = Ki;
                robotControl.Kd = Kd;
                enable ();
            }
            else
                RobotErrorMessage ( "Must enter numbers" );
            break;
        default:
            RobotErrorMessage ( "Routine Not Implemented Yet" );
    }
}

/*
***************************************************************
*** M e n u E n t e r B a n g B a n g P a r a m s ( ) ********
***************************************************************

This function provides the user with a text entry window
    for loading the bang-bang motion parameters.

Passed Parameters:
        double *pos         - desired relative position (inches)
        double *time        - total move time (sec)
        double *tacc        - acceleration time (sec)

Return Value:
        none

*/
int MenuEnterBangBangParams ( double *pos, double *time, double *tacc )
{
    WINDOW *win;
    char posStr[64], timeStr[64], taccStr[64], temp[255];

sprintf ( posStr,  "%.3lf", *pos );
    sprintf ( timeStr, "%.3lf", *time );
    sprintf ( taccStr, "%.3lf", *tacc );

if ( (win=establish_window(10,10,10,30)) != NULL)
    {
```

```
        set_colors(win,ALL,BLUE,WHITE,BRIGHT);
        set_title(win, " Bang-Bang Move Parameters ");
        display_window(win);
        establish_field(win,2,2,"  Rel Pos: _____ (in)", posStr, 'A' );
        establish_field(win,2,3," Move Time: _____ (sec)", timeStr, 'A' );
        establish_field(win,2,4,"  Acc Time: _____ (sec)", taccStr, 'A' );
        data_entry(win);
        delete_window(win);
        if ( !sscanf(posStr,"%lf",pos) ) return(FALSE);
        if ( !sscanf(timeStr,"%lf",time) ) return(FALSE);
        if ( !sscanf(taccStr,"%lf",tacc) ) return(FALSE);
        sprintf ( temp, "Pos=%.3lf, Time=%.3lf, Acc=%.3lf : OK (y/n) ?",
                  *pos, *time, *tacc );
        if ( RobotYesNoWin(temp) )
            return (TRUE);
    }
    return (FALSE);
} void hide_intros(){};
void display_intros(){};

/*
***************************************************************
***************************************************************
***                                            **********
***   M O V E . C                              **********
***                                            **********
***   Pat Jensen                               **********
***   Biomedical Engineering                   **********
***   Northwestern University                  **********
***                                            **********
***   April 14, 1993                           **********
***                                            **********
***************************************************************
***************************************************************

This file contains routines for calculating motion
    profiles for robot motion.

*/

/* Included files */
#include <stdio.h>
#include <stdlib.h>
#include <math.h>
#include <string.h>
#include "robot.h"
#include "move.h"
#include "debug.h"

/*
*******************************************************************
*** J o y s t i c k M o v e ( )                        *********
*******************************************************************

This function performs the robot inverse kinematics and control law
    to yield the reference motor state.

Passed Parameters:
            RobotControl *robotControl

Return Value:
            int                    - TRUE on success
*/ int JoystickMove ( RobotControl *robotControl )
{
    int ii, jj, kk;
    double Lv[3][6];            /* Array of Six Virtual Leg Vectors   */
    double R01[3][3];           /* Product of Two arrays R0*R1        */
    double Rt[3][3];            /* Product of Three arrays Rc*R0*R1   */
    double Ap_Base[3][6];       /* Attachments to Platform (Base Coords)*/
    double Ljjx2, Ljjy2, Ljjz;  /* Temporary leg-length variables     */
    double c0, c1, s0, s1;      /* Cosine and Sine terms              */
    double E[6];                /* Actuator Extensions                */
    double oldPos[NUM_JOINTS];  /* Save last position to calculate vel */
    double temp;

/* Save the old position    */
```

```
    for ( ii=0; ii<NUM_JOINTS; ii++ )
        oldPos[ii] = robotControl->desiredPos[ii];

/* calculate the cosine and sine of the joystick inputs */
    c0=cos(M_PI*(robotControl->joyY)/360.0);
    c1=cos(M_PI*(robotControl->joyX)/360.0);
    s0=sin(M_PI*(robotControl->joyY)/360.0);
    s1=sin(M_PI*(robotControl->joyX)/360.0);

/* Multiply the two rotation matrices */
    R01[0][0]=c0;   R01[0][1]=-s0*s1;  R01[0][2]=-s0*c1;
    R01[1][0]=0;    R01[1][1]=c1;      R01[1][2]=-s1;
    R01[2][0]=s0;   R01[2][1]=0;       R01[2][2]=c0*c1;

/* Multiply composite by previous product */
    for(ii=0; ii<=2; ii++)
        for(jj=0; jj<=2; jj++)
            Rt[ii][jj] = (robotControl->Rc[ii][0])*R01[0][jj] +
                         (robotControl->Rc[ii][1])*R01[1][jj] +
                         (robotControl->Rc[ii][2])*R01[2][jj];

/* Copy resultant to composite */
    for(ii=0; ii<=2; ii++)
        for(jj=0; jj<=2; jj++)
            robotControl->Rc[ii][jj]=Rt[ii][jj];

/* Get platform attachments in base coords */
    for(ii=0; ii<=2; ii++)
        for(jj=0; jj<NUM_JOINTS; jj++)
            Ap_Base[ii][jj] = Rt[ii][0]*(robotControl->Ap_Prime[0][jj]) +
                              Rt[ii][1]*(robotControl->Ap_Prime[1][jj]) +
                              Rt[ii][2]*(robotControl->Ap_Prime[2][jj]) +
                              robotControl->Tbp[ii];

/* Calculate leg vectors */
    for(jj=0; jj<NUM_JOINTS; jj++)
    {
        Ljjx2 = (Ap_Base[0][jj] - (robotControl->Ab_Base[0][jj])) *
                (Ap_Base[0][jj] - (robotControl->Ab_Base[0][jj]));
        Ljjy2 = (Ap_Base[1][jj] - (robotControl->Ab_Base[1][jj])) *
                (Ap_Base[1][jj] - (robotControl->Ab_Base[1][jj]));
        Ljjz  = (Ap_Base[2][jj] - (robotControl->Ab_Base[2][jj]));
        temp  = FIXED_LEG_LENGTH_SQUARED - Ljjx2 - Ljjy2;
        if ( temp >= (double)0.0 )
        {
            E[jj] = Ljjz - sqrt(temp);
            robotControl->desiredPos[jj] = E[jj] * RAD_PER_INCH;
            robotControl->desiredVel[jj] = (robotControl->desiredPos[jj] -
                                            oldPos[jj])/CONTROL_INTERVAL;
#ifdef DEBUG
    if(jj==0) DebugCollectData(robotControl->desiredPos[jj],robotControl->actualPos[jj],robotContr
#endif
        }
        else
            return(FALSE);
    } return(TRUE);
}

/*
**********************************************************
***  B a n g B a n g M o v e ( )                **********
**********************************************************

This function performs a 2nd order move (bang-bang)
    between two points.

Passed Parameters:
        RobotMove *move       - Current move data
        RobotControl *control - Current control data Return Value:
        int                   - TRUE on success

*/
int BangBangMove ( RobotMove *move, RobotControl *control )
{
    int i;
    double h, Z, t, Time1;
```

```
/* Set time equal to smaller variable name for readability */
t = move->time;

/* Subtract tacc from the travel time */
Time1 = (move->moveTime) - (move->tacc);

/* Loop on the number of joints */
for ( i=0; i<NUM_JOINTS; i++ )
{
    /* If less than start time, sit at point A */
    if ( t <= 0.0 )
    {
        control->desiredPos[i] = move->posA[i];
        control->desiredVel[i] = 0.0;
        control->desiredAcc[i] = 0.0;
    }
    /* Bang start acceleration to linear segment */
    else if ( t <= move->tacc )
    {
        Z = ((move->posB[i])-(move->posA[i]))/Time1;
        control->desiredPos[i] = Z*t*t/(2.0*(move->tacc))+(move->posA[i]);
        control->desiredVel[i] = Z*t/(move->tacc);
        control->desiredAcc[i] = Z/(move->tacc);
    }
    /* Linear segment between A and B */
    else if ( t <= Time1 )
    {
        Z = ((move->posB[i])-(move->posA[i]))/Time1;
        control->desiredPos[i] = Z*t-Z*(move->tacc)/2.0-(move->posA[i]);
        control->desiredVel[i] = Z;
        control->desiredAcc[i] = 0.0;
    }
    /* Bang stop acceleration to linear segment */
    else if ( t <= Time1+move->tacc )
    {
        Z = ((move->posB[i])-(move->posA[i]))/Time1;
        h = Time1 + move->tacc - t;
        control->desiredPos[i] = (-1.0)*Z*h*h/(2.0*(move->tacc))+(move->posB[i]);
        control->desiredVel[i] = Z*h/(move->tacc);
        control->desiredAcc[i] = (-1.0)*Z/(move->tacc);
    }
    /* Time beyond movement envelope, freeze at point B */
    else
    {
        control->desiredPos[i] = move->posB[i];
        control->desiredVel[i] = 0.0;
        control->desiredAcc[i] = 0.0;
        control->moveType=MOVE_FIXED;
    }

}

/* Increment the time if the move is not finished */
move->time += CONTROL_INTERVAL;

return(TRUE);
}

/*
***************************************************************
*** R o b o t L o a d M o v e ( )              **********
***************************************************************

This function loads the passed position, time, and
    acceleration values into the movement data structure.
    This function loads the same information into all joints.

Passed Parameters:
        RobotMove *move         - Current move data
        double pos              - desired destination (inches)
        double time             - desired travel time (sec)
        double acc              - acceleration time (sec)

Return Value:
        int                     - TRUE on success

*/
int RobotLoadBangBangMove ( RobotControl *robotControl,
                            RobotMove *robotMove,
                            double pos,
                            double time,
                            double acc)
```

```
{
    int i;

/* Check for valid data */
    if ( time <= 0.0 ) return (FALSE);
    if ( acc < 0.1 ) return (FALSE);
    if ( time < 2.0*acc ) return (FALSE);

for ( i=0; i<NUM_JOINTS; i++ )
    {
        if ( robotControl->desiredPos[i]+pos*RAD_PER_INCH > 1.0*RAD_PER_INCH ||
             robotControl->desiredPos[i]+pos*RAD_PER_INCH < -1.0*RAD_PER_INCH )
              return (FALSE);
    } for ( i=0; i<NUM_JOINTS; i++ )
    {
        robotMove->posA[i] = robotControl->actualPos[i];
        robotMove->posB[i] = robotMove->posA[i] + pos*RAD_PER_INCH;
    } robotMove->moveTime = time;
    robotMove->tacc = acc;
    robotMove->time = 0.0;

return (TRUE);
}

/*
*************************************************************
*** R o b o t I n i t M o v e ( )              **********
*************************************************************

This function intializes the bang-bang move data
    structure so the pid loop doesn't blow up.

Passed Parameters:

RobotMove *move         - Current move data

Return Value:
        int                     - TRUE on success

*/
void RobotInitMove ( RobotMove *robotMove )
{
    int i;

for ( i=0; i<NUM_JOINTS; i++ )
    {
        robotMove->posA[i] = 0.0;
        robotMove->posB[i] = 0.0;
    } robotMove->moveTime = 10.0;
    robotMove->tacc = 1.0;
    robotMove->time = 0.0;
}

/*
*************************************************************
*** F r e e M o v e ( )                        **********
*************************************************************

This function sets the current actual position to the desired
    position. This is a simple method of providing constant control
    update of position while keeping the torque at zero.

Passed Parameters:
        RobotControl *robotControl     - Current move data

Return Value:
        int                            - TRUE on success

*/
int FreeMove ( RobotControl *robotControl )
{
    int i;
    for ( i=0; i<NUM_JOINTS; i++ )
```

```c
    {
        robotControl->desiredPos[i] = robotControl->actualPos[i];
        robotControl->desiredVel[i] = robotControl->actualVel[i];
        robotControl->desiredAcc[i] = robotControl->actualAcc[i];
    }
    return (TRUE);
}

/*
***************************************************************
*** R o b o t F r e e z e ( )                    **********
***************************************************************

This function copies the actual position into the
    desired position and sets the desired veocity and
    acceleration to zero.  It has the effect of freezing
    the robot in it's current position.

Passed Parameters:
        RobotControl *robotControl     - Current control data Return Value:

int                            - TRUE on success

*/
int RobotFreeze ( RobotControl *robotControl )
{
    int i;
    for ( i=0; i<NUM_JOINTS; i++ )
    {
        robotControl->desiredPos[i] = robotControl->actualPos[i];
        robotControl->desiredVel[i] = 0.0;
        robotControl->desiredAcc[i] = 0.0;
    }
    return (TRUE);
}

/*
***************************************************************
*** R e a d J o y s t i c k F i l e ( )          **********
***************************************************************

This function simulates the use of a joystick by entering
    the joystick variables from a file.

Passed Parameters:
        RobotControl *robotControl     - Current control data Return Value:
        int                            - TRUE on success

*/
int ReadJoystickFile ( RobotControl *robotControl, char *path )
{
    FILE *file;
    char temp[32],temp2[32];
    int i;

/* Clear the data arrays */
    for ( i=0; i<MOVE_FILE_MAX; i++ );
    {
        robotControl->joyDataX[i] = 0;
        robotControl->joyDataY[i] = 0;
    }

/* Open the joystick file */
    if ( (file=fopen(path,"rt")) == FALSE )
        return (FALSE);

/* Make sure it is a move file */
    fgets ( temp, 32, file );
    temp[strlen(temp)-1] = NULL;
    if ( strcmp(temp,MOVE_FILE_DESC)  )
    {
        RobotErrorMessage ( "Selected file is not a move file" );
        return (FALSE);
    }

/* Read the joystick scale */
```

```c
    fgets ( temp, 32, file );
    if ( !sscanf(temp,"%d",&(robotControl->joyScale)) )
        return (FALSE);

/* Read data until end of file or max size is reached */
    i = 0;
    while ( !feof(file) && i<MOVE_FILE_MAX )
    { fgets ( temp, 32, file );
        if ( sscanf(temp,"%d,%d",
                &(robotControl->joyDataX[i]),
                &(robotControl->joyDataY[i])) != 2 )
        {
            fclose(file);
            return(FALSE);
        }
        i++;
    }

/* Close the file */
    robotControl->joyNum = i-1;
    robotControl->joyNum--;
    robotControl->joyIndex = 0;
    fclose(file);
    return (TRUE);
}

/*
***************************************************************
*** U p d a t e J o y s t i c k F r o m F i l e ( ) *********
***************************************************************

This function uses the data loaded from the joystick
    file as joystick input.

Passed Parameters:
        RobotControl *robotControl     - Current control data Return Value:
        int                            - TRUE on success

*/
int UpdateJoystickFromFile ( RobotControl *robotControl )
{
    int i;
    int index, scale, num;
    int *dataX, *dataY;

/* Copy data to shorter variable names */
    index = robotControl->joyIndex;
    scale = robotControl->joyScale;
    num   = robotControl->joyNum;
    dataX = robotControl->joyDataX;
    dataY = robotControl->joyDataY;

/* Move the robot until the move is done */
    if ( (index/scale) < num )
    {
        if ( index/scale == 0 )
        {
            robotControl->joyX = (((double)dataX[0])/1000.0)/(double)scale;
            robotControl->joyY = (((double)dataY[0])/1000.0)/(double)scale;
        }
        else
        {
            robotControl->joyX = ((((double)dataX[index/scale])/1000.0) -
                                (((double)dataX[index/scale-1])/1000.0))/
                                (double)scale;
            robotControl->joyY = ((((double)dataY[index/scale])/1000.0) -
                                (((double)dataY[index/scale-1])/1000.0))/
                                (double)scale;
        }
        robotControl->joyZ = 0.0;

robotControl->joySense = 1.0;
        robotControl->joyOn = 1;
        robotControl->joyIndex++;
        return (TRUE);
    }
```

```
        else
        {
            /* Set motion to freeze */
            for ( i=0; i<NUM_JOINTS; i++ )
            {
                robotControl->desiredPos[i] = robotControl->actualPos[i];
                robotControl->desiredVel[i] = 0.0;
                robotControl->desiredAcc[i] = 0.0;
            }
            robotControl->moveType=MOVE_FIXED;
            return(FALSE);
        }
    } int RobotMoveReference ( RobotControl *robotControl,
                         RobotMove *robotMove )
{
    int i;

for ( i=0; i<NUM_JOINTS; i++ )
    {
        robotMove->posA[i] = robotControl->actualPos[i];
        robotMove->posB[i] = 0.0;
    } robotMove->moveTime = 10.0;
    robotMove->tacc = 1.0;
    robotMove->time = 0.0;

return (TRUE);
} int RobotMoveCalibration ( RobotControl *robotControl,
                           RobotMove *robotMove )
{
    int i;

for ( i=0; i<NUM_JOINTS; i++ )
    {
        robotMove->posA[i] = robotControl->actualPos[i];
        robotMove->posB[i] = -RAD_PER_INCH;
    } robotMove->moveTime = 10.0;
    robotMove->tacc = 1.0;
    robotMove->time = 0.0;

return (TRUE);
}

/* --------------- ibmpc.c -------------- */

/*
 * Low-level functions addressing DOS, BIOS & PC Hardware
 */
#include <dos.h>
#include <string.h>
#include <bios.h>
#include "qwindow.h"

extern int  *winErrorFlag;
extern void (*winErrorHandler)();

static union REGS rg;
static struct SREGS sg;

/* ----------- position the cursor ------------ */
void cursor(int x, int y)
{
    vmode();
    rg.x.ax = 0x0200;
    rg.x.dx = ((y << 8) & 0xff00) + x;
    int86(0x10, &rg, &rg);
}

/* ----------- return the cursor position ------------ */
void curr_cursor(int *x, int *y)
{
    vmode();
    rg.x.ax = 0x0300;
    int86(0x10, &rg, &rg);
    *x = rg.h.dl;
```

```c
        *y = rg.h.dh;
}

/* ---------- set cursor type --------------- */
void set_cursor_type(int t)
{
        rg.x.ax = 0x0100;
        rg.x.bx = 0;
        rg.x.cx = t;
        int86(0x10, &rg, &rg);
}
char attrib = 7;

/* ------------- clear the screen ------------- */
void clear_screen()
{
        cursor(0, 0);
        rg.h.al = ' ';
        rg.h.ah = 9;
        rg.x.bx = attrib;
        rg.x.cx = 2000;
        int86(0x10, &rg, &rg);
}

/* ----------- return the video mode ----------- */
int vmode()
{
        rg.h.ah = (char) 15;
        int86(0x10, &rg, &rg);
        return rg.h.al;
} int snowing = 0;      /* 1 for retrace test, 0 for none */

/* --------- return the video refresh address -------- */
unsigned video_address()
{
        static char copyr [7];

snowing = 0;
        /* ---- test for MDA ---- */
        if (vmode() == 7)
                return 0xb000;
        /* ---- test for EGA ---- */
        rg.x.ax = 0x1130;
        rg.h.bh = 0;
        rg.h.dl = 0xff;
        int86(0x10, &rg, &rg);
        if (rg.h.dl == 255)
                snowing++;
        /* ----- test for COMPAQ ---- */
        segread(&sg);
        movedata(0xf000, 0xffea, sg.ds, (unsigned) copyr, 6);
        copyr[6] = '\0';
        snowing &= strcmp(copyr, "COMPAQ");
        vmode();
        return 0xb800 + 0x100 * rg.h.bh;
}

/* -------- test for scroll lock -------- */
int scroll_lock()
{
        rg.x.ax = 0x0200;
        int86(0x16, &rg, &rg);
        return rg.h.al & 0x10;
} void (*helpfunc)(void);
int keyhit(void);
int helpkey = 0;
int helping = 0;

/* ------------- get a keyboard character --------------- */
int get_char()
{
    int c;

while (1)
    {
        /* Check for errors */
        if ( *winErrorFlag )
            (*winErrorHandler)();
```

```c
/* Check for key press */
if (kbhit())
{
    c = bioskey(0);
    if ((c & 0xff) == 0)
        c = ((c >> 8) & 0xff) | 128;
    else
        c &= 0xff;
    if (c == helpkey && helpfunc)
    {
        if (!helping)
        {
            helping = 1;
            (*helpfunc)();
            helping = 0;
            continue;
        }
        break;
    }
} return c;
} void setdta(char far *dta)
{
    rg.h.ah = 0x1a;
    rg.x.dx = FP_OFF(dta);
    sg.ds = FP_SEG(dta);
    int86x(0x21, &rg, &rg, &sg);
} char far *getdta(void)
{
    static char far *dta;

rg.h.ah = 0x2f;
    int86x(0x21, &rg, &rg, &sg);
    (*((unsigned *)&(dta) + 1)) = sg.es;
    (*((unsigned *)&(dta))) = rg.x.bx;
    return dta;
}
```

```
/*
*************************************************************
*************************************************************
***                                                **********
*** P I D . C                                      **********
***                                                **********
*** Pat Jensen                                     **********
*** Biomedical Engineering                         **********
*** Northwestern University                        **********
***                                                **********
*** March 20, 1993                                 **********
***                                                **********
*************************************************************
*************************************************************

This file is a collection of routines to perform pid control
   for a generic robot.

*/

/* Included files */
#include <math.h>
#include "robot.h"
#include "pid.h"

/*
*************************************************************
*** P I D ( )                                      **********
*************************************************************

This performs the control loop for robot motion. It
  incorporates a pid controller with dynamic compensation
```

```
    for gravity and inertia.  Position is in radians, velocity
    in radians/sec and motor output in tourque(Nm).

Passed Parameters:
        RobotControl *control   - Robot control data

Return Value:
        int                     - Returns TRUE or FALSE
*/
int PID ( RobotControl *control )
{
    int i;
    double Kd, Kp, temp;

/* Loop on the number of joints */
    for ( i=0; i<NUM_JOINTS; i++ )
    {
        /* Calculate Torque in mNm */
        control->motorOutput[i] =
                control->Kd *
                        ((control->desiredVel[i])-(control->actualVel[i])) +
                control->Kp *
                        ((control->desiredPos[i])-(control->actualPos[i]));

/* Place software limit on torque */
        if ( control->motorOutput[i] < (-MOTOR_MAX_T) )
            control->motorOutput[i] = (-MOTOR_MAX_T);
        if ( control->motorOutput[i] > MOTOR_MAX_T )
            control->motorOutput[i] = MOTOR_MAX_T;

} return (TRUE);
}

/*
***************************************************************
***************************************************************
***                                              **********
***  R O B O T . C                               **********
***                                              **********
***  Pat Jensen                                  **********
***  Biomedical Engineering                      **********
***  Northwestern University                     **********
***                                              **********
***  March 20, 1993                              **********
***                                              **********
***************************************************************
***************************************************************

This file contains miscellaneous high level routines
    that are called from the menu.

*/

/* Included system files */
#include <stdio.h>
#include <stdlib.h>
#include <sys\timeb.h>
#include <dos.h>

/* Included program files */
#include "robot.h"
#include "debug.h"
#include "control.h"
#include "adc\adc.h"
#include "resolver\resolver.h"
#include "encoder\encoder.h"
#include "dac\dac.h"
#include "move.h"
#include "pid.h"
#include "int.h"
#include "menu.h"

/*
***************************************************************
*** R o b o t I n i t ( )                        **********
***************************************************************
```

```
    This function initializes all the hardware cards in
    the system.

*/
int RobotInit ( RobotControl *robotControl, RobotMove *robotMove )
{
    /* Initialize the ADC */
    if ( !RobotInitADC(robotControl) )
        return ( ERROR_ADC );

/* Initialize the static kinematic parameters */
    RobotKinParamInit ( robotControl );

/* Initialize the movement data structure */
    RobotInitMove ( robotMove );

/* Initialize the DAC */
    if ( !RobotInitDAC(robotControl) )
        return ( ERROR_DAC );

/* Initialize the resolvers */
    if ( !RobotInitResolvers(robotControl,-1.0) )
        return ( ERROR_RESOLVER );

/* Set the movement type to freeze */
    RobotFreeze ( robotControl );
    robotControl->moveType = MOVE_FIXED;

return ( ERROR_NONE );
}

/*
***************************************************************
*** R o b o t S e t C o n t r o l P a r a m s ( )   **********
***************************************************************

This function sets the control parameters of the system
    to those that are passed.

*/
void RobotSetControlParams ( RobotControl *robotControl,
                             double Kp,
                             double Kd,
                             double velFilter )
{
    robotControl->Kp = Kp;
    robotControl->Kd = Kd;
    robotControl->velFilter = velFilter*CONTROL_INTERVAL;
}

/*
***************************************************************
*** R o b o t K i n P a r a m I n i t ( )           **********
***************************************************************

This function initializes the static kinematic data
    matrices.

*/
void RobotKinParamInit ( RobotControl *rc )
{
    rc->Tbp[0]=0.8;
    rc->Tbp[1]=0.0;
    rc->Tbp[2]=4.191;

rc->Ap_Prime[0][0] =  0.558063;
    rc->Ap_Prime[0][1] =  0.558063;
    rc->Ap_Prime[0][2] =  0.839753;
    rc->Ap_Prime[0][3] =  1.73113;
    rc->Ap_Prime[0][4] =  1.73113;
    rc->Ap_Prime[0][5] =  0.839753;
    rc->Ap_Prime[1][0] = -0.72781;
    rc->Ap_Prime[1][1] =  0.72781;
    rc->Ap_Prime[1][2] =  0.95781;
    rc->Ap_Prime[1][3] =  0.23000;
    rc->Ap_Prime[1][4] = -0.23000;
    rc->Ap_Prime[1][5] = -0.95781;
    rc->Ap_Prime[2][0] = -2.65927;
```

```
    rc->Ap_Prime[2][1] = -2.65927;
    rc->Ap_Prime[2][2] = -2.37758;
    rc->Ap_Prime[2][3] = -1.48620;
    rc->Ap_Prime[2][4] = -1.48620;
    rc->Ap_Prime[2][5] = -2.37758;
    rc->Ab_Base[0][0] = -0.97319;
    rc->Ab_Base[0][1] = -0.97319;
    rc->Ab_Base[0][2] =  0.28741;
    rc->Ab_Base[0][3] =  0.68578;
    rc->Ab_Base[0][4] =  0.68578;
    rc->Ab_Base[0][5] =  0.28741;
    rc->Ab_Base[1][0] = -0.23000;
    rc->Ab_Base[1][1] =  0.23000;
    rc->Ab_Base[1][2] =  0.95781;
    rc->Ab_Base[1][3] =  0.72781;
    rc->Ab_Base[1][4] = -0.72781;
    rc->Ab_Base[1][5] = -0.95781;
    rc->Ab_Base[2][0] =  0.0;
    rc->Ab_Base[2][1] =  0.0;
    rc->Ab_Base[2][2] =  0.0;
    rc->Ab_Base[2][3] =  0.0;
    rc->Ab_Base[2][4] =  0.0;
    rc->Ab_Base[2][5] =  0.0;

rc->Rc[0][0] =  0.707107;
    rc->Rc[0][1] =  0.0;
    rc->Rc[0][2] =  0.707107;
    rc->Rc[1][0] =  0.0;
    rc->Rc[1][1] =  1.0;
    rc->Rc[1][2] =  0.0;
    rc->Rc[2][0] = -0.707107;
    rc->Rc[2][1] =  0.0;
    rc->Rc[2][2] =  0.707107;
/*
***************************************************************
***************************************************************
***                                                 **********
***   C O N T R O L . H                             **********
***                                                 **********
***   Pat Jensen                                    **********
***   Biomedical Engineering                        **********
***   Northwestern University                       **********
***                                                 **********
***   March 20, 1993                                **********
***                                                 **********
***************************************************************
***************************************************************

*/ ifndef CONTROL_H
define CONTROL_H

/* Function Prototypes */
void ControlLoop ( RobotMove *robotMove, RobotControl *robotControl );

#endif  CONTROL_H
                        /*
***************************************************************
***************************************************************
***                                                 **********
***   D E B U G . H                                 **********
***                                                 **********
***   Pat Jensen                                    **********
***   Biomedical Engineering                        **********
***   Northwestern University                       **********
***                                                 **********
***   March 20, 1993                                **********
***                                                 **********
***************************************************************
***************************************************************

*/ ifndef DEBUG_H
define DEBUG_H

/* Function Prototypes */
void DebugCollectData (double,double,double,double,double,double);
void DebugPrintData ();
int DebugEnterPIDParams ( double *Kp, double *Ki, double *Kd );

#endif  DEBUG_H
```

```
/*
***************************************************************
***************************************************************
***                                                 **********
***   I N T . H                                     **********
***                                                 **********
***   Pat Jensen                                    **********
***   Biomedical Engineering                        **********
***   Northwestern University                       **********
***                                                 **********
***   March 20, 1993                                **********
***                                                 **********
***************************************************************
***************************************************************

This file defines values needed to handle hardware
     interrupts on the PC bus.

*/ ifndef INT_H
define INT_H

/* 8259A Hardware interrupt enable flags */
#define HW_IRQ0        0x01
#define HW_IRQ1        0x02
#define HW_IRQ2        0x04
#define HW_IRQ3        0x08
#define HW_IRQ4        0x10
#define HW_IRQ5        0x20
#define HW_IRQ6        0x40
#define HW_IRQ7        0x50

/* Software interrupt vectors for hardware interrupts */
#define VEC_IRQ0       0x08
#define VEC_IRQ1       0x09
#define VEC_IRQ2       0x0A
#define VEC_IRQ3       0x0B
#define VEC_IRQ4       0x0C
#define VEC_IRQ5       0x0D
#define VEC_IRQ6       0x0E
define VEC_IRQ7       0x0F /* Interrupts to use for this handler */
define INT_NUM        HW_IRQ5
#define VEC_NUM        VEC_IRQ5

/* 8259A Interrupt controller I/O addresses */
#define INT_CTRL_PORT  0x20
#define INT_MASK_PORT  0x21

/* 8259A End of Interrupt command */
define END_OF_INT     0x20 void interrupt IntHandler ( void );
int LoadIntHandler ( void );
int RestoreIntHandler ( void );
int EnableIRQ ( int IntNum );
int DisableIRQ ( int IntNum );
int EndOfInterrupt ( void );

#endif INT_H

/*
***************************************************************
***************************************************************
***                                                 **********
***   M E N U . H                                   **********
***                                                 **********
***   Pat Jensen                                    **********
***   Biomedical Engineering                        **********
***   Northwestern University                       **********
***                                                 **********
***   March 20, 1993                                **********
***                                                 **********
***************************************************************
***************************************************************

This file contains menu information for operating the
     event driven menu system for the robot.
```

```
*/ ifndef MENU_H
define MENU_H void MoveMenu(int,int);
void DebugMenu(int,int);
void RobotMenu ();
void RobotErrorMessage ( char * );
void RobotErrorHandler ();
void RobotMenuPowerOn ();
void RobotMenuPowerOff ();
void RobotAbort ();
int  MenuEnterBangBangParams ( double *pos, double *time, double *tacc );

/* Define variables only available to the MENU.C file */
#ifdef  MENU_C

WINDOW *backwind;
int fn_index;
char *fn_str[]={"","",NULL};
char help_name[9];

char *robotStrings[] =
{
        "Exit",
        "Power Up",
        "Power Down",
        NULL
};
void *robotFuncs[] =
{
        NULL,
        RobotMenuPowerOn,
        RobotMenuPowerOff,
        NULL
};

char *moveStrings[] =
{
        "Freeze",
        "Free",
        "Joystick",
        "Joystick File",
        "Bang-Bang",
        NULL
};

void *moveFuncs[] =
{
        MoveMenu,
        MoveMenu,
        MoveMenu,
        MoveMenu,
        MoveMenu,
        NULL
};

char *debugStrings[] =
{
        "Robot",
        "PID",
        "A/D",
        "D/A",
        "Resolver",
        "Encoder",
        NULL
};
void *debugFuncs[] =
{
        DebugMenu,
        DebugMenu,
        DebugMenu,
        DebugMenu,
        DebugMenu,
        DebugMenu,
        NULL
};

void *abortFuncs[] =
```

```
{
        RobotAbort,
        NULL
};

MENU menu[] =
{
        "ROBOT",
        robotStrings,
        NULL,
        robotFuncs, "MOVE",
        moveStrings,
        NULL,
        moveFuncs, "ABORT",
        NULL,
        NULL,
        abortFuncs, "DEBUG",
        debugStrings,
        NULL,
        debugFuncs,

NULL,
        NULL,
        NULL,
        NULL
};

endif  MENU_C endif  MENU_H

/*
*************************************************************
*************************************************************
***                                                ***********
***  M O V E . H                                   ***********
***                                                ***********
***  Pat Jensen                                    ***********
***  Biomedical Engineering                        ***********
***  Northwestern university                       ***********
***                                                ***********
***  March 20, 1993                                ***********
***                                                ***********
*************************************************************
*************************************************************

*/ ifndef MOVE_H
define MOVE_H

/* Calculate Bang-Bang Movement Profile */
int JoystickMove ( RobotControl *robotControl );
int FreeMove ( RobotControl *robotControl );
int RobotFreeze ( RobotControl *robotControl );
int ReadJoystickFile ( RobotControl *robotControl, char *path );
int UpdateJoystickFromFile ( RobotControl *robotControl );
int BangBangMove ( RobotMove *move, RobotControl *control );
int RobotLoadBangBangMove ( RobotControl *robotControl,
                            RobotMove *robotMove,
                            double pos,
                            double time,
                            double acc);
int RobotMoveCalibration ( RobotControl *robotControl,
                            RobotMove *robotMove );
int RobotMoveReference ( RobotControl *robotControl,
                            RobotMove *robotMove );
void RobotInitMove ( RobotMove *robotMove );

#endif
```

```
/*
**************************************************************
**************************************************************
***                                                 **********
***    P I D . H                                    **********
***                                                 **********
***    Pat Jensen                                   **********
***    Biomedical Engineering                       **********
***    Northwestern Univeristy                      **********
***                                                 **********
***    March 20, 1993                               **********
***                                                 **********
**************************************************************
**************************************************************

This file contains constants and function prototypes
    for use by the pid.c file.

*/ ifndef PID_H
define PID_H int PID ( RobotControl *control );

endif PID_H

/*
**************************************************************
**************************************************************
***                                                 **********
***    R O B O T . H                                **********
***                                                 **********
***    Pat Jensen                                   **********
***    Biomedical Engineering                       **********
***    Northwestern University                      **********
***                                                 **********
***    March 20, 1993                               **********
***                                                 **********
**************************************************************
**************************************************************

This file contains all the data structure definitions
    needed to control the robot.

*/

/* Miscellaneous definitions */
#define NUM_JOINTS              6
#define NUM_ADC_CHANS           7
#define CONTROL_INTERVAL        .001            /* sec          */
#define DEFAULT_VEL_BW          1000            /* Hz           */
#define DEFAULT_KP              10              /* mNm per rad  */
#define DEFAULT_KD              0.10            /* mNm per r/s  */
#define RAD_PER_INCH            50.26548245     /* rad/inch     */
#define INCH_PER_RAD            0.019894368     /* inch/rad     */
#define MOTOR_MAX_VEL           60.0            /* rad/sec      */
#define MOTOR_MAX_T             13.03           /* mNm          */
#define MOTOR_LIMIT_T           13.03           /* mNm          */
#define MOTOR_ACC_LIMIT_T       0.5             /* mNm          */
#define MOTOR_MAX_ACC           10.6            /* rad/s^2      */
define MOTOR_T_PER_A           2.6069759       /* mNm per Amp  */ define MOVE_FILE_MASK          "C:\\SOURCE\\MOVEDATA\\*.*"
define MOVE_FILE_PATH          "C:\\SOURCE\\MOVEDATA"
#define MOVE_FILE_DESC          "<Robot Move File>"
define MOVE_FILE_MAX           1000 define FIXED_LEG_LENGTH_SQUARED        4                                       /* inc define MOVE_FIXED              1
define MOVE_FREE               2
#define MOVE_JOYSTICK           3
#define MOVE_JOYSTICK_FILE      4
define MOVE_BANG_BANG          5 define DEBUG_ROBOT             1
define DEBUG_PID               2 define TRUE                    1
define FALSE                   0

/* #define DEBUG                                 /* Debug flag  */
```

```c
/* Data structure for moving the robot */
typedef struct robot_move
{
    double posA[NUM_JOINTS];            /* Starting position (rev)      */
    double posB[NUM_JOINTS];            /* Ending position (rev)        */
    double moveTime;                    /* Time length of move (sec)    */
    double time;                        /* Actual time (sec)            */
    double tacc;                        /* Acceleration time (sec)      */
} RobotMove;

/* Data structure for controlling the robot */
typedef struct robot_control
{
    double  J[NUM_JOINTS];              /* Maximum inertias for joints  */
    double  Wn;                         /* Natural frequency of robot   */
    double  Kp;                         /* Proportional Gain            */
    double  Ki;                         /* Integral Gain                */
    double  Kd;                         /* Differential Gain            */
    double  velFilter;                  /* Velocity filter coefficient  */
    double  Rc[3][3];                   /* Composite matrix             */
    double  desiredPos[NUM_JOINTS];     /* Desired robot position (rev) */
    double  desiredVel[NUM_JOINTS];     /* Desired robot velocity       */
    double  desiredAcc[NUM_JOINTS];     /* Desired robot acceleration   */
    double  actualPos[NUM_JOINTS];      /* Actual robot position (rev)  */
    double  actualVel[NUM_JOINTS];      /* Actual robot velocity        */
    double  actualAcc[NUM_JOINTS];      /* Actual robot acceleration    */
    double  resolverOffset[NUM_JOINTS]; /* Calibration offset           */
    double  robotForce[NUM_ADC_CHANS];  /* Strain gauge forces          */
    double  motorOutput[NUM_JOINTS];    /* Current output to motors     */
    int     calibrated;                 /* Robot home succesful         */
    int     moveType;                   /* Type of current move         */
    int     powerOn;                    /* EM Stop Status (1=STOPPED)   */
    int     powerEnable;                /* EM Stop Control (1=STOP)     */
    double  joyX;                       /* Joystick X value             */
    double  joyY;                       /* Joystick Y value             */
    double  joyZ;                       /* Joystick Z value             */
    double  joySense;                   /* Joystick Sensitivity         */
    int     joyOn;                      /* Joystick Active (1=ON)       */
    double  Tbp[3];                     /* Translation vector base->puncture */
    double  Ap_Prime[3][6];             /* Platform attachments in endpt coords */
    double  Ab_Base[3][6];              /* Base attachments in base coords */
    int     joyDataX[MOVE_FILE_MAX];    /* Pointer to X joystick data   */
    int     joyDataY[MOVE_FILE_MAX];    /* Pointer to Y joystick data   */
    int     joyIndex;                   /* Present joystick entry       */
    int     joyNum;                     /* Number of joystick entries   */
    int     joyScale;                   /* Time scale (update every x clocks) */
} RobotControl;

/* Error values correspond to error strings listed below */
#define ERROR_NONE      0
#define ERROR_ADC       1
#define ERROR_RESOLVER  2
#define ERROR_ENCODER   3
#define ERROR_MOVE      4
#define ERROR_PID       5
#define ERROR_DAC       6
#define ERROR_EMSTOP    7
#define ERROR_VELOCITY  8
#define ERROR_DEBUG     9

/* Global Variables */
#ifdef ROBOT_MAIN
  RobotControl robotControl;
  RobotMove robotMove;
  int robotError;
  char *errorString[] = { "No Error",
                          "ADC Error",
                          "Resolver Error",
                          "Encoder Error",
                          "Move Error",
                          "PID Error",
                          "DAC Error",
                          "EM Stop",
                          "Max Velocity Exceeded",
                          "Debug Length Exceeded",
                          0};
#else
  extern RobotControl robotControl;
  extern RobotMove robotMove;
  extern int robotError;
  extern char *errorString[];
#endif
```

```
/* Prototype Defintions */
void RobotSetControlParams ( RobotControl *robotControl,
                             double Kp, double Kd, double Ka );
int  RobotInit ( RobotControl *robotControl, RobotMove *robotMove );
void RobotKinParamInit ( RobotControl *robotControl );
```

```
/*
****************************************************************
****************************************************************
***                                                  **********
***   A D C . C                                      **********
***                                                  **********
***   Pat Jensen                                     **********
***   Biomedical Engineering                         **********
***   Northwestern University                        **********
***   March 20, 1993                                 **********
***                                                  **********
****************************************************************
****************************************************************

This file includes functions used to control and
    acquire data for the analog to digital converter
    card listed below:

CIO-AD16JR-AT
        Computer Boards, INC.
        44 Wood Ave.
        Mansfield, MA  02048
        (508) 261-1123
        FAX:  261-1094

*/

/* Included Files */
#include <stdio.h>;
#include <stdlib.h>
#include <dos.h>
#include "robot.h"
#include "adc\adc.h"

/* Global Variables */
ADC adc1, adc2;

#define VEL_SCALE    .030679688
#define VEL_OFFSET   62.832

/*
****************************************************************
*** R o b o t I n i t A D C ( )               **********
****************************************************************

This function initializes the ADC card for the following
    data acquisition scheme.
        - No interrupt
        - Data passed upon request
        - no DMA The ADC will eventually happen on an interrupt from the pacer
    clock on the ADC card.

*/
int RobotInitADC ( RobotControl *robotControl )
{
    /* Initialize ADC #1 */
    ADC_Create ( &adc1, ADC1_BASE );
    ADC_Reset ( &adc1 );
    ADC_DisableInt ( &adc1 );
    ADC_DisableDMA ( &adc1 );
    ADC_InternalTrigger ( &adc1 );
    ADC_SetMuxChans ( &adc1, 0, NUM_ADC_CHANS-1 );

/* Initialize ADC #2 */

ADC_Create ( &adc2, ADC2_BASE );
    ADC_Reset ( &adc2 );
    ADC_DisableInt ( &adc2 );
    ADC_DisableDMA ( &adc2 );
    ADC_InternalTrigger ( &adc2 );
    ADC_SetMuxChans ( &adc2, 0, 0 );

return (TRUE);
}
```

```
/*
************************************************************
*** R o b o t R e a d A D C ( )                ***********
************************************************************
*/
int RobotReadADC ( RobotControl *robotControl )
{
    int i, Chan, Value, oldVel;
    unsigned int Hold;

/* Read the strain gauge data */
/*   for ( i=0; i<NUM_ADC_CHANS; i++ )
    {
        while ( ADC_Busy(&adc1) );
        Hold = (unsigned int)inportb(adc1.base+ADC_AD_LOW);
        Hold |= ((unsigned int)inportb(adc1.base+ADC_AD_HIGH)<<8);
        robotControl->robotForce[Hold&0x000F] = (double)(Hold>>4);
    } */

/* Copy the joystick sensitivity to the proper place */
    robotControl->joySense = robotControl->robotForce[ADC_JOYSENSE_CHAN];

/* Read digital input lines ( EMStop and Joystick On/Off ) */
    Value = ADC_ReadDigitalInput ( &adc1 );
    robotControl->powerOn = !BCHK(Value,POWER_ON_BIT);
    robotControl->joyOn   =  BCHK(Value,JOY_ON_BIT);

/* Write the digital output lines */
    if ( !robotControl->powerEnable || !robotControl->powerOn )
    {
        robotControl->powerOn = FALSE;
        robotControl->powerEnable = FALSE;
        RobotPower ( robotControl, FALSE );
    }
    else
        RobotPower ( robotControl, TRUE );

return (TRUE);
}

/*
************************************************************
*** R o b o t P o w e r ( )                    ***********
************************************************************
*/
int RobotPower ( RobotControl *robotControl, int powerOn )
{
    /* Set the TTL output to enable power amps if powerOn=TRUE */
    if ( powerOn )
    {
        ADC_SetDigitalOutput ( &adc1, POWER_ENABLE_BIT );
        robotControl->powerEnable=TRUE;
    }
    else {
        ADC_ClearDigitalOutput ( &adc1, POWER_ENABLE_BIT );
        robotControl->powerEnable=FALSE;
    } return (TRUE);
}

/*
************************************************************
*** R o b o t S i g n a l I n t ( )            ***********
************************************************************
*/
int RobotSignalInt ( int signalOn )
{
    /* Set the TTL output to signal an interrupt occured */
    if ( signalOn )
        ADC_SetDigitalOutput ( &adc1, INT_SIGNAL_BIT );
    else
        ADC_ClearDigitalOutput ( &adc1, INT_SIGNAL_BIT );

return (TRUE);
}
```

```c
/*
***************************************************************
*** R o b o t S t a r t P a c e r ( )              **********
***************************************************************
*/
int RobotStartPacer ()
{
    ADC_StartPacer ( &adc1, 5 );
    return(TRUE);
}

/*
***************************************************************
*** R o b o t S t o p P a c e r ( )                **********
***************************************************************
*/
int RobotStopPacer ()
{
    ADC_StopPacer ( &adc1 );
    return(TRUE);
}

/*
***************************************************************
*** R o b o t C l e a r I n t ( )                  **********
***************************************************************
*/
int RobotClearInt ()
{
    ADC_ClearINT ( &adc1 );
    return(TRUE);
}

/*
***************************************************************
*** A D C _ S t a r t P a c e r ( )                **********
***************************************************************
*/
void ADC_StartPacer ( ADC *adc, int intLevel )
{
    ADC_SetIntLevel ( adc, intLevel );
    ADC_ClearINT ( adc );
    ADC_EnableInt ( adc );
    adc->control |= 0x03;         /* Convert on pacer int */
    outportb ( adc->base+ADC_CONTROL, (unsigned char)adc->control );
    outportb ( adc->base+ADC_CLOCK_CTRL, 0xB6 );
    outportb ( adc->base+ADC_CLOCK_DAT2, 0xFA );
    outportb ( adc->base+ADC_CLOCK_DAT2, 0x00 );
    outportb ( adc->base+ADC_CLOCK_CTRL, 0x76 );
    outportb ( adc->base+ADC_CLOCK_DAT1, 0x04 );
    outportb ( adc->base+ADC_CLOCK_DAT1, 0x00 );
    outportb ( adc->base+ADC_PACER_CTRL, 0x01 );
}

/*
***************************************************************
*** A D C _ S t o p P a c e r ( )                  **********
***************************************************************
*/
void ADC_StopPacer ( ADC *adc )
{
    ADC_DisableInt ( adc );
    ADC_ClearINT ( adc );
    adc->control &= 0xFC;         /* Convert on software trigger only */
    outportb ( adc->base+ADC_CONTROL, (unsigned char)adc->control );
    outportb ( adc->base+ADC_PACER_CTRL, 0x00 );
}

/*
***************************************************************
*** A D C _ S e t I n t L e v e l ( )              **********
***************************************************************
*/
void ADC_SetIntLevel ( ADC *adc, int Level )
{
```

```c
    Level = Border ( Level, 2, 7 );
    adc->control &= 0x8F; /* Clear level bits */
    adc->control |= ((Level&0x07)<<4);
    outportb ( adc->base+ADC_CONTROL, (unsigned char)adc->control );
}

/*
***************************************************************
*** A D C _ C r e a t e ( )                        **********
***************************************************************
*/
void ADC_Create ( ADC *adc, int Addr )
{
    adc->control = 0;
    adc->digital = 0;
    adc->base = Addr;
}

/*
***************************************************************
*** A D C _ R e s e t ( )                          **********
***************************************************************
*/
void ADC_Reset ( ADC *adc )
{
    adc->control = 0;
    outportb ( (adc->base)+ADC_CONTROL, (unsigned char)(adc->control) );
    adc->digital = 0;
    outportb ( (adc->base)+ADC_DIO, (unsigned char)(adc->digital) );
    ADC_SetMuxChans ( adc, 0, 15 );
}

/*
***************************************************************
*** A D C _ R e a d V a l u e ( )                  **********
***************************************************************
*/
void ADC_ReadValue ( ADC *adc, int *Value, int *Chan )
{
    unsigned int Hold;

ADC_SoftwareTrigger (adc);
    while ( ADC_Busy(adc) );
    Hold = (unsigned int)inportb((adc->base)+ADC_AD_LOW);
    Hold |= (((unsigned int)inportb((adc->base)+ADC_AD_HIGH))<<8);
    *Chan = (int)(Hold&0x000F);
    *Value = (int)((Hold&0xFFF0)/16);
}

/*
***************************************************************
*** A D C _ S e t D i g i t a l O u t p u t ( )    **********
***************************************************************
*/
void ADC_SetDigitalOutput ( ADC *adc, int Bit )
{
    adc->digital |= BSET(Bit);
    outportb ( (adc->base)+ADC_DIO, (unsigned char)(adc->digital) );
}

/*
***************************************************************
*** A D C _ C l e a r D i g i t a l O u t p u t ( ) **********
***************************************************************
*/
void ADC_ClearDigitalOutput ( ADC *adc, int Bit )
{
    adc->digital &= BCLR(Bit);
    outportb ( adc->base+ADC_DIO, (unsigned char)adc->digital );
}

/*
***************************************************************
*** A D C _ R e a d D i g i t a l I n p u t ( )    **********
***************************************************************
```

```
*/
int ADC_ReadDigitalInput ( ADC *adc )
{
   return ( (int)inportb(adc->base+ADC_DIO) );
}

/*
****************************************************************
*** A D C _ S e t M u x C h a n s ( )           **********
****************************************************************
*/
void ADC_SetMuxChans ( ADC *adc, int Begin, int End )
{
   unsigned char Value;

Begin = Border ( Begin, 0, 15 );
   End = Border ( End, 0, 15 );
   Value = (((unsigned char)End<<4)|(unsigned char)Begin);
   outportb ( adc->base+ADC_MUX, Value );
}

/*
****************************************************************
*** A D C _ S o f t w a r e T r i g g e r ( )   **********
****************************************************************
*/
void ADC_SoftwareTrigger ( ADC *adc )
{
  outportb ( adc->base+ADC_AD_LOW, (unsigned char)0 );
}

/*
****************************************************************
*** A D C _ B u s y ( )                         **********
****************************************************************
*/
int ADC_Busy ( ADC *adc )
{
  return ( (int)BCHK(inportb(adc->base+ADC_STATUS),7) );
}

/*
****************************************************************
*** A D C _ C h e c k U n i p o l a r ( )       **********
****************************************************************
*/
int ADC_CheckUnipolar ( ADC *adc )
{
  return ( (int)BCHK(inportb(adc->base+ADC_STATUS),6) );
}

/*
****************************************************************
*** A D C _ C h e c k 1 6 C h a n ( )           **********
****************************************************************
*/
int ADC_Check16Chan ( ADC *adc )
{
  return ( (int)BCHK(inportb(adc->base+ADC_STATUS),5) );
}

/*
****************************************************************
*** A D C _ C h e c k F o r I N T ( )           **********
****************************************************************
*/
int ADC_CheckForINT ( ADC *adc )
{
  return ( (int)BCHK(inportb(adc->base+ADC_STATUS),4) );
}

/*
****************************************************************
*** A D C _ M U X C h a n ( )                   **********
****************************************************************
```

```c
*/
int ADC_MUXChan ( ADC *adc )
{
   return ( (int)inportb(adc->base+ADC_STATUS)&0x0F );
}

/*
***************************************************************
*** A D C _ C l e a r I N T ( )                    **********
***************************************************************
*/
void ADC_ClearINT ( ADC *adc )
{
   outportb ( adc->base+ADC_STATUS, (unsigned char)0 );
}

/*
***************************************************************
*** A D C _ E n a b l e I n t ( )                  **********
***************************************************************
*/
void ADC_EnableInt ( ADC *adc )
{
   adc->control |= BSET(7);
   outportb ( adc->base+ADC_CONTROL, (unsigned char)adc->control );
}

/*
***************************************************************
*** A D C _ D i s a b l e I n t ( )                **********
***************************************************************
*/
void ADC_DisableInt ( ADC *adc )
{
   adc->control &= BCLR(7);
   outportb ( adc->base+ADC_CONTROL, (unsigned char)adc->control );
}

/*
***************************************************************
*** A D C _ E n a b l e D M A ( )                  **********
***************************************************************
*/
void ADC_EnableDMA ( ADC *adc )
{
   adc->control &= BSET(2);
   outportb ( adc->base+ADC_CONTROL, (unsigned char)adc->control );
}

/*
***************************************************************
*** A D C _ D i s a b l e D M A ( )                **********
***************************************************************
*/
void ADC_DisableDMA ( ADC *adc )
{
   adc->control &= BCLR(2);
   outportb ( adc->base+ADC_CONTROL, (unsigned char)adc->control );
}

/*
***************************************************************
*** A D C _ I n t e r n a l T r i g g e r ( )      **********
***************************************************************
*/
void ADC_InternalTrigger ( ADC *adc )
{
   adc->control &= BCLR(1);
   outportb ( adc->base+ADC_CONTROL, (unsigned char)adc->control );
}

/*
***************************************************************
*** A D C _ E x t e r n a l T r i g g e r ( )      **********
***************************************************************
```

```c
*/
void ADC_ExternalTrigger ( ADC *adc )
{
   adc->control &= BSET(1);
   outportb ( adc->base+ADC_CONTROL, (unsigned char)adc->control );
}

/*
***************************************************************
*** B o r d e r ( )                                  **********
***************************************************************
*/
int Border ( int Value, int Min, int Max )
{
  if ( Value < Min )
    Value = Min;
  if ( Value > Max )
    Value = Max;
  return ( Value );
}

/*
***************************************************************
***************************************************************
***                                                  **********
***   A D C . H                                      **********
***                                                  **********
*** Pat Jensen                                       **********
*** Biomedical Engineering                           **********
*** Northwestern University                          **********
*** March 20, 1993                                   **********
***                                                  **********
***************************************************************
***************************************************************

This file includes definitions and and function
    prototypes used in the driver for the analog to
    digital converter card listed below:

CIO-AD16JR-AT
        Computer Boards, INC.
        44 Wood Ave.
        Mansfield, MA   02048
        (508) 261-1123
        FAX:  261-1094

*/ ifndef ADC_H
define ADC_H define TRUE            1
define FALSE           0
define ERR             -1 define BSET(x) (1<<x)
define BCLR(x) (~(1<<x))
#define BCHK(v,b) (v&BSET(b)?TRUE:FALSE)

#define ADC1_BASE            0x320
#define ADC2_BASE            0x340
#define ADC_JOYSENSE_CHAN    6      /* Chan # for joysense, others force */
#define POWER_ON_BIT         1      /* ADC digital input                 */
#define JOY_ON_BIT           3      /* ADC digital input                 */
#define POWER_ENABLE_BIT     0      /* ADC digital output                */
#define INT_SIGNAL_BIT       1      /* Signal an interrupt occured       */

/* Define Port Offsets from the base */
#define ADC_AD_LOW       0
#define ADC_AD_HIGH      1
#define ADC_MUX          2
#define ADC_DIO          3
#define ADC_STATUS       8
#define ADC_CONTROL      9
#define ADC_PACER_CTRL   10
#define ADC_GAIN         11
#define ADC_CLOCK_DAT0   12
#define ADC_CLOCK_DAT1   13
#define ADC_CLOCK_DAT2   14
#define ADC_CLOCK_CTRL   15
```

```
/* Define the ADC structure */
typedef struct adcStruct
{
    int base;
    int control;
    int digital;
} ADC;

/* High Level Routines */
int RobotInitADC ( RobotControl *robotControl );
int RobotReadADC ( RobotControl *robotControl );
int RobotPower ( RobotControl *robotControl, int powerOn );
int RobotSignalInt ( int signalOn );
int RobotStartPacer ();
int RobotStopPacer ();
int RobotClearInt ();

/* Mid Level Routines */
void ADC_Create ( ADC *adc, int Addr );
void ADC_Reset ( ADC * );
void ADC_ReadValue ( ADC *, int *Value, int *Chan );
void ADC_SetDigitalOutput ( ADC *, int Bit );
void ADC_ClearDigitalOutput ( ADC *, int Bit );
int ADC_ReadDigitalInput ( ADC * );

/* Low Level Routines */
void ADC_SetMuxChans ( ADC *, int Begin, int End );
void ADC_SoftwareTrigger ( ADC * );
int  ADC_Busy ( ADC * );
int  ADC_CheckUnipolar ( ADC * );
int  ADC_Check16Chan ( ADC * );
int  ADC_CheckForINT ( ADC * );
void ADC_ClearINT ( ADC * );
void ADC_EnableInt ( ADC * );
void ADC_DisableInt ( ADC * );
int  ADC_MUXChan ( ADC * );
void ADC_SetIntLevel ( ADC *, int Level );
void ADC_EnableDMA ( ADC * );
void ADC_DisableDMA ( ADC * );
void ADC_InternalTrigger ( ADC * );
void ADC_ExternalTrigger ( ADC * );
void ADC_StartPacer ( ADC *adc, int intLevel );
void ADC_StopPacer ( ADC *adc );
int  Border ( int Value, int Min, int Max );

#endif ADC_H
/*
*************************************************************
*************************************************************
***                                                ***********
***   D A C . C                                    ***********
***                                                ***********
***   Pat Jensen                                   ***********
***   Biomedical Engineering                       ***********
***   Northwestern University                      ***********
***                                                ***********
***   March 20, 1993                               ***********
***                                                ***********
*************************************************************
*************************************************************

This file contains routines for initializing and writing
    data to the CIO-DAC16 board.

*/

/* Included files */
#include <stdio.h>
#include <dos.h>
#include "robot.h"
#include "dac\dac.h"

/*
*************************************************************
*** R o b o t I n i t D A C ( )                    **********
*************************************************************

This function initializes the D/A converter board for use
    with the robot.
```

```c
*/
int RobotInitDAC ( RobotControl *robotControl )
{
    int i;

/* Set the voltage output (motor torque) to zero */
    for ( i=0; i<NUM_JOINTS; i++ )
        robotControl->motorOutput[i] = 0.0;

/* Update the DAC */
    return ( RobotWriteDAC(robotControl) );
}

/*
*************************************************************
*** R o b o t W r i t e D A C ( )              **********
*************************************************************

This function writes the motor output values located in
    the robotControl->motorOutput array (range is -10.0 to +10.0)
    to the DAC board.

*/
int RobotWriteDAC ( RobotControl *robotControl )
{
    int i, Value, addr;

/* Start with DAC 0 at base address */
    addr = DAC_BASE;
    /* Load the D/A registers */
    for ( i=0; i<NUM_JOINTS; i++ )
    {
        /* Calculate 12 bit value (0-4095) from +/- 10 input */
        Value = (int)((robotControl->motorOutput[i])*DAC_SCALE+DAC_OFFSET);
        /* Write low byte */
        outportb ( addr++, (unsigned char)(Value&0xFF) );
        /* Write high nibble */
        outportb ( addr++, (unsigned char)((Value&0xF00)/0xFF) );
    }

/* Read from DAC to update all registers at once */
    inportb ( DAC_BASE );

return (TRUE);
}

/*
*************************************************************
*************************************************************
***                                             **********
*** D A C . H                                   **********
***                                             **********
*** Pat Jensen                                  **********
*** Biomedical Engineering                      **********
*** Northwestern University                     **********
***                                             **********
*** March 20, 1993                              **********
***                                             **********
*************************************************************
*************************************************************

This file contains definitions and function prototypes for
    the CIO-DAC16 card. The card should be jumpered for an
    address of 0x360, wait state on, XFER set for all channels,
    and analog output of +/- 10v.

*/ ifndef DAC_H
define DAC_H

/* DAC Scaling factors - Converts desired Torque(mNm) to dac voltage */
#define DAC_SCALE       157.0842
#define DAC_OFFSET      2048.0

/* DAC Addresses */
#define DAC_BASE        0x360
```

```
/* Function Prototypes */
int RobotInitDAC ( RobotControl *robotControl );
int RobotWriteDAC ( RobotControl *robotControl );

#endif RESOLVER_H
```

What is claimed is:

1. A device for precision positioning of an instrument within a biotic structure through a hole in an exterior wall of the biotic structure, said device comprising:
- a structural member of the instrument extending through the hole of the biotic structure at a puncture point with the instrument disposed on the structural number at a first end within the biotic structure;
- an instrument holding means disposed at a second end of the structural member outside the biotic structure for retaining an instrument at a predetermined angle and for adjusting and positioning said instrument at a desired location;
- selectively moveable support means for supporting said instrument holding means;
- actuator means for activating said selectively moveable support means;
- input means for generating electronic positioning signals responsive in realtime to indicia, provide by a user, of desired movement of said instrument; and
- means for controlling said selectively moveable support means by determining the correct movement of said selectively moveable support means responsive to said electronic positioning signals, said control means being in electronic communication with said actuator means and said input means, said control means being adapted to activate said actuator means to position said selectively moveable support means while maintaining the structural member substantially stationary in a plane of the exterior wall at the puncture point.

2. The device as defined in claim 1 further comprising sensing means for determining instrument position.

3. The device as defined in claim 1 wherein said instrument holding means, said instrument manipulating means and said selectively moveable support means are replaced by a micromanipulator mechanism.

4. The device as defined in claim 1 wherein said selectively moveable support means comprises an attachment platform plate comprising a plurality of support legs depending therefrom, said support legs comprising a first end and a second end opposing said first end.

5. The device as defined in claim 4 wherein said first end of said support legs are pivotally, movably coupled to said attachment platform plate and said second end of said support legs are pivotally, movably coupled to an actuator extension arm, said actuator extension arm being secured to said actuator means along the actuator extension arm's other end.

6. The device as defined in claim 4 wherein each of said support legs is coupled to said actuator means, and said actuator means comprises a motor activated ball screw and linear slider mechanism.

7. The device as defined in claim 4 further comprising six of said support legs coupled to six of said actuator means providing the user with six degrees of freedom of movement for said selective support means.

8. The device as defined in claim 1 wherein said input means comprises a joystick device activated by movement of a surgeon's hands.

9. The device as defined in claim 8 wherein said joystick device includes means for adjustably setting a sensitivity for the surgeon's hand motions.

10. The device as defined in claim 9 further including a plunge action actuator for axial displacement of said instrument.

11. The device as defined in claim 1 wherein said controlling means comprises a personal computer.

12. The device as defined in claim 1 wherein said controlling means is configured to determine the correct movement of said selectively moveable support means when said instrument is constrained at a given point in space.

13. The device as defined in claim 1 further comprising means for substantially synchronously operating said controlling means and said selectively moveable support means in response to the user's indicia at said input means.

14. A device for precision positioning of an instrument within a biotic structure through a hole in an exterior wall of the biotic structure, said device comprising:
- a structural member of the instrument extending through the hole of the biotic structure at a puncture point with the instrument disposed on the structural member at a first end within the biotic structure;
- an instrument holding means disposed at a second end of the structural member outside the biotic structure for retaining an instrument at a predetermined angle;
- selectively moveable support means for supporting said instrument holding means, said moveable support means being rotatably coupled to said instrument holding means;
- actuator means for activating said selectively moveable support means;
- input means for generating electronic positioning signals responsive in realtime to indicia, inputted by a user, of desired movement of said instrument manipulating means; and
- means for controlling said selectively moveable support means by determining a correct movement of said selectively moveable support means responsive to said positioning signals, said control means being in communication with said actuator means and said input means, said control means being adapted to activate said actuator means to position said selectively moveable support means while maintaining the structural member substantially stationary in the plane of the exterior wall at the puncture point.

15. The device as defined in claim 14 further including sensing means for determining where said instrument is positioned at a given time.

16. The device as defined in claim 14 wherein said instrument holding means and said selectively moveable support means are each components of a micromanipulator mechanism.

17. The device as defined in claim 14 wherein said selectively moveable support means comprises an attachment platform plate comprising a plurality of support legs depending therefrom, said support legs comprising a first end and a second end opposing said first end.

18. The device as defined in claim 17 wherein said first end of said support legs are pivotally, movably coupled to said attachment platform plate and said second end of said support legs are pivotally, movably coupled to an actuator extension arm, said actuator extension arm being secured to said actuator means along the actuator extension arm's other end.

19. The device as defined in claim 17 wherein each of said support legs is coupled to said actuator means, and said actuator means comprises a motor activated ball screw and linear slider mechanism.

20. The device as defined in claim 17 further comprising six of said support legs coupled to six of said actuator means which provides the user with six degrees of freedom of movement for said selective support means.

21. The device as defined in claim 14 further including means for rotational displacement of said instrument in a clockwise or counter-clockwise direction.

22. The device as defined in claim 14 wherein said input means comprises a joystick device activated by movement of a surgeon's hands.

23. The device as defined in claim 22 wherein said joystick device includes means for adjustably setting a sensitivity for the surgeon's hand motions.

24. The device as defined in claim 14 further including a plunge action actuator for axial displacement of said instrument.

25. The device as defined in claim 14 further comprising means for substantially synchronously operating said controlling means and said selectively moveable support means in response to the user's indicia at said input means.

26. The device as defined in claim 14 wherein said predetermined angle further comprises a 45° angle.

27. A device for precision positioning of an instrument within a biotic structure through a hole in an exterior wall of the biotic structure, said device comprising:
a structural member of the instrument extending through the hole of the biotic structure at a puncture point with the instrument disposed on the structural member at a first end within the biotic structure
an instrument holding means disposed at a second end of the structural member outside the biotic structure for retaining an instrument at a predetermined angle;
an attachment platform for supporting said instrument holding means;
a plurality of support legs comprising a first end and a second end opposite said first end, said first end of said support legs being pivotally, movably coupled to said attachment platform;
actuator means for selectively positioning said support legs and said attachment platform, said actuator means being pivotally, movably coupled to said second end of said support legs;
input means for generating electronic positioning signals responsive in realtime to indicia, inputted by a user, of desired movement of said instrument; and
means for controlling the positioning of said attachment platform while maintaining the structural member substantially stationary in a plane of the exterior wall at the puncture point comprising means for determining a correct movement of said support legs responsive to said positioning signals, said control means being in communication with said actuator means and said input means, said control means being adapted to activate said actuator means to position said attachment platform.

28. The device as defined in claim 27 wherein said actuator means comprises a motor activated ball screw and linear slider mechanism.

29. The device as defined in claim 27 wherein a ball and socket joint assembly is utilized to couple said first end of said support legs to said attachment platform and said second end of said support legs to said actuator means.

30. The device as defined in claim 27 further comprising at least six of said support legs coupled to six of said actuator means providing the user with six degrees of freedom of movement for positioning said attachment platform.

31. The device as defined in claim 27 further comprising means for rotating said instrument in a clockwise or counter-clockwise direction about an axis of the structural member.

* * * * *